(12) United States Patent
Fregoso et al.

(10) Patent No.: US 12,115,364 B2
(45) Date of Patent: *Oct. 15, 2024

(54) ELECTRICAL DISCHARGE IRRIGATOR APPARATUS AND METHOD

(71) Applicant: G & H Technologies, LLC, Kalispell, MT (US)

(72) Inventors: Gilbert Fregoso, Deer Park, WA (US); Brad B. Heckerman, Kalispell, MT (US)

(73) Assignee: Endo-Logic, LLC, Kalispell, MT (US)

( * ) Notice: Subject to any disclaimer, the term of this patent is extended or adjusted under 35 U.S.C. 154(b) by 922 days.

This patent is subject to a terminal disclaimer.

(21) Appl. No.: 17/157,639

(22) Filed: Jan. 25, 2021

(65) Prior Publication Data
US 2021/0162202 A1    Jun. 3, 2021

Related U.S. Application Data

(63) Continuation of application No. 16/351,039, filed on Mar. 12, 2019, now Pat. No. 10,898,705, which is a
(Continued)

(51) Int. Cl.
*A61C 17/02* (2006.01)
*A61B 18/04* (2006.01)
(Continued)

(52) U.S. Cl.
CPC .......... *A61N 1/0448* (2013.01); *A61B 18/042* (2013.01); *A61C 1/06* (2013.01); *A61C 1/07* (2013.01); *A61C 3/00* (2013.01); *A61C 3/03* (2013.01); *A61C 5/40* (2017.02); *A61C 5/50* (2017.02); *A61C 17/0202* (2013.01); *A61C 17/16* (2013.01); *A61C 17/20* (2013.01); *A61C 19/063* (2013.01); *A61L 2/025* (2013.01);
(Continued)

(58) Field of Classification Search
CPC ..... A61C 17/02; A61C 17/0202; A61C 15/00; A61C 19/063; A61N 1/44; A61N 1/0548; A61B 2218/002; A61B 2218/003
See application file for complete search history.

(56) References Cited

U.S. PATENT DOCUMENTS 3,889,160 A * 6/1975 Cobarg .................. F23Q 2/285
361/256
5,254,121 A * 10/1993 Manevitz ......... A61B 17/22022
606/29
(Continued)

*Primary Examiner* — Justine R Yu
*Assistant Examiner* — Christopher E Miller
(74) *Attorney, Agent, or Firm* — Heslin Rothenberg Farley & Mesiti PC

(57) ABSTRACT

An electrical discharge irrigation device includes a power source to produce power of a first voltage, a circuit coupled to the power source to convert the power of the first voltage to power of a second voltage where the second voltage is higher than the first voltage, a trigger to activate the circuit, an igniter coupled to the circuit to produce a spike, an electrical charge storage component coupled to the igniter the electrical charge storage component becoming conductive and storing an electrical charge after receiving the spike, and an output tip. The output tip includes an electrode and insulating material as an outer layer.

17 Claims, 19 Drawing Sheets

Related U.S. Application Data continuation of application No. 14/427,469, filed as application No. PCT/US2012/070080 on Dec. 17, 2012, now Pat. No. 10,232,164.

(60) Provisional application No. 61/699,568, filed on Sep. 11, 2012.

(51) Int. Cl.

| | | |
|---|---|---|
| *A61C 1/06* | (2006.01) | |
| *A61C 1/07* | (2006.01) | |
| *A61C 3/00* | (2006.01) | |
| *A61C 3/03* | (2006.01) | |
| *A61C 5/40* | (2017.01) | |
| *A61C 5/50* | (2017.01) | |
| *A61C 17/16* | (2006.01) | |
| *A61C 17/20* | (2006.01) | |
| *A61C 19/06* | (2006.01) | |
| *A61L 2/025* | (2006.01) | |
| *A61L 2/10* | (2006.01) | |
| *A61L 2/14* | (2006.01) | |
| *A61L 2/18* | (2006.01) | |
| *A61N 1/04* | (2006.01) | |
| *A61N 1/05* | (2006.01) | |
| *A61N 1/30* | (2006.01) | |
| *A61N 1/32* | (2006.01) | |
| *A61N 1/44* | (2006.01) | |
| *A61N 5/06* | (2006.01) | |
| *A61L 2/00* | (2006.01) | |
| *A61L 2/22* | (2006.01) | |

(52) U.S. Cl.
CPC .............. *A61L 2/10* (2013.01); *A61L 2/14* (2013.01); *A61L 2/18* (2013.01); *A61N 1/04* (2013.01); *A61N 1/0548* (2013.01); *A61N 1/306* (2013.01); *A61N 1/325* (2013.01); *A61N 1/44* (2013.01); *A61N 5/0603* (2013.01); *A61B 2217/007* (2013.01); *A61L 2/00* (2013.01); *A61L 2/0088* (2013.01); *A61L 2/22* (2013.01); *A61L 2202/25* (2013.01); *A61N 2005/0606* (2013.01); *A61N 2005/0661* (2013.01); *F04C 2270/0421* (2013.01)

(56) References Cited

U.S. PATENT DOCUMENTS

| | | | | |
|---|---|---|---|---|
| 5,464,513 A * | 11/1995 | Goriachev | ............ | B01J 19/088 422/186.21 |
| 5,567,153 A * | 10/1996 | Foulkes | ................. | B23P 15/26 433/119 |
| 5,572,135 A * | 11/1996 | Owens | .................... | F02P 17/12 324/382 |
| 5,928,505 A * | 7/1999 | Inakagata | ............... | A61C 17/02 320/108 |
| 6,186,963 B1 * | 2/2001 | Schwarze | ............. | G10K 15/06 601/4 |
| 7,678,069 B1 * | 3/2010 | Baker | ................ | A61B 18/1206 604/22 |
| 2006/0269900 A1 * | 11/2006 | Paschke | ............. | A61C 1/0015 433/119 |
| 2007/0160958 A1 * | 7/2007 | Belikov | ............... | A61C 19/066 433/215 |
| 2007/0208334 A1 * | 9/2007 | Woloszko | ........... | A61B 18/148 606/41 |
| 2007/0244425 A1 * | 10/2007 | Pond | ..................... | A61M 1/774 604/27 |
| 2008/0097425 A1 * | 4/2008 | Truckai | ................ | A61B 18/042 606/41 |
| 2008/0255498 A1 * | 10/2008 | Houle | ................ | A61C 17/0208 604/20 |
| 2008/0280260 A1 * | 11/2008 | Belikov | ............... | A46B 11/002 433/32 |
| 2009/0130622 A1 * | 5/2009 | Bollinger | ............. | A61C 1/0046 433/29 |
| 2009/0143718 A1 * | 6/2009 | Jiang | .................... | A61B 18/042 604/23 |
| 2009/0258324 A1 * | 10/2009 | Yoshioka | ........... | A61C 17/0208 433/91 |
| 2010/0009310 A1 * | 1/2010 | Aleksandrovskiy | ..... | A61C 5/46 433/32 |
| 2011/0183284 A1 * | 7/2011 | Yamanaka | ........... | H05H 1/2406 433/32 |
| 2012/0237893 A1 * | 9/2012 | Bergheim | ................ | A61C 5/40 433/81 |
| 2012/0295218 A1 * | 11/2012 | Moll | .................... | A61C 17/222 433/32 |
| 2013/0164705 A1 * | 6/2013 | Tanaka | ................. | A61C 19/063 433/80 |
| 2015/0056567 A1 * | 2/2015 | Fregoso | ................. | A61C 19/06 433/29 |

\* cited by examiner

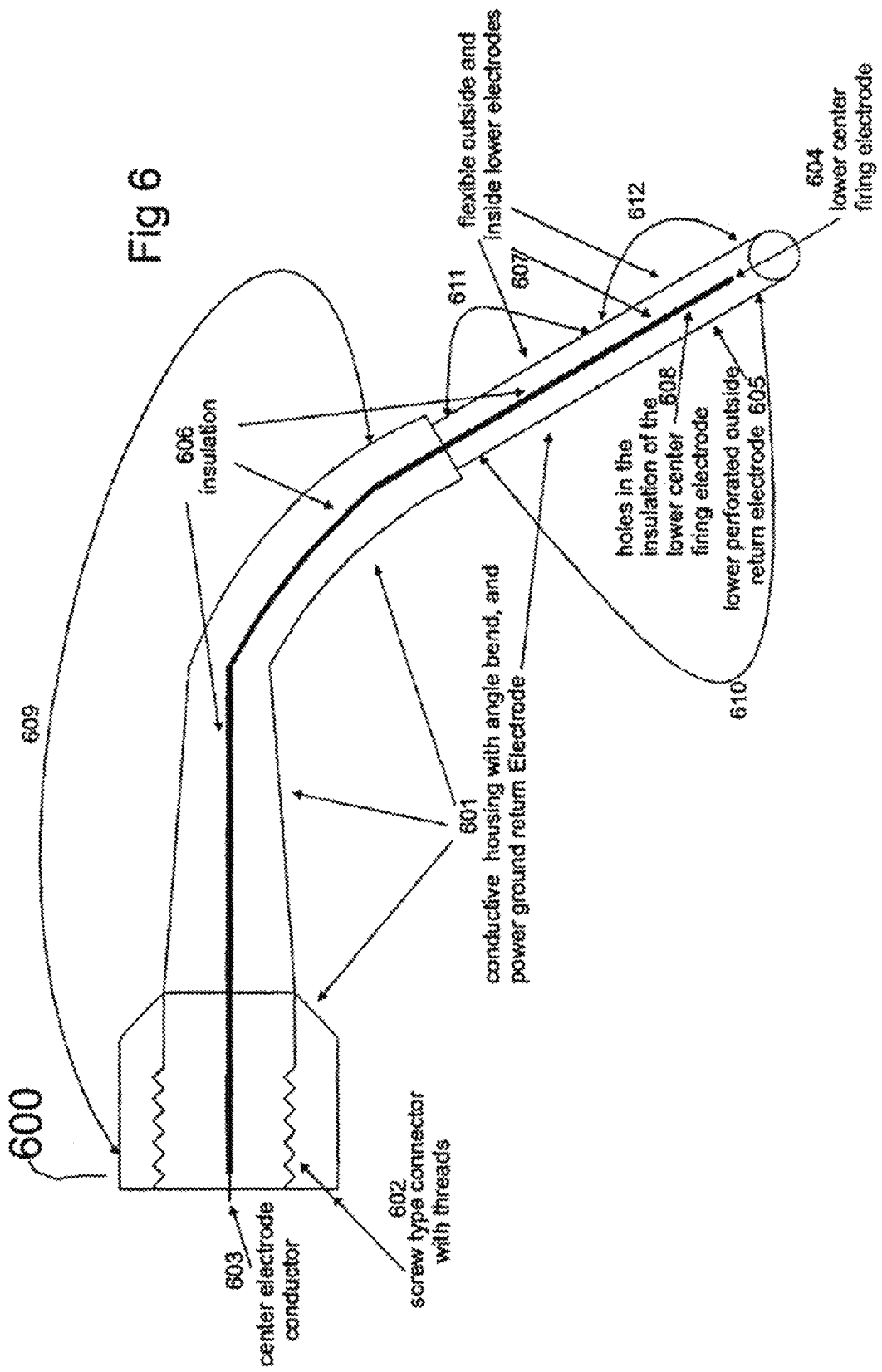

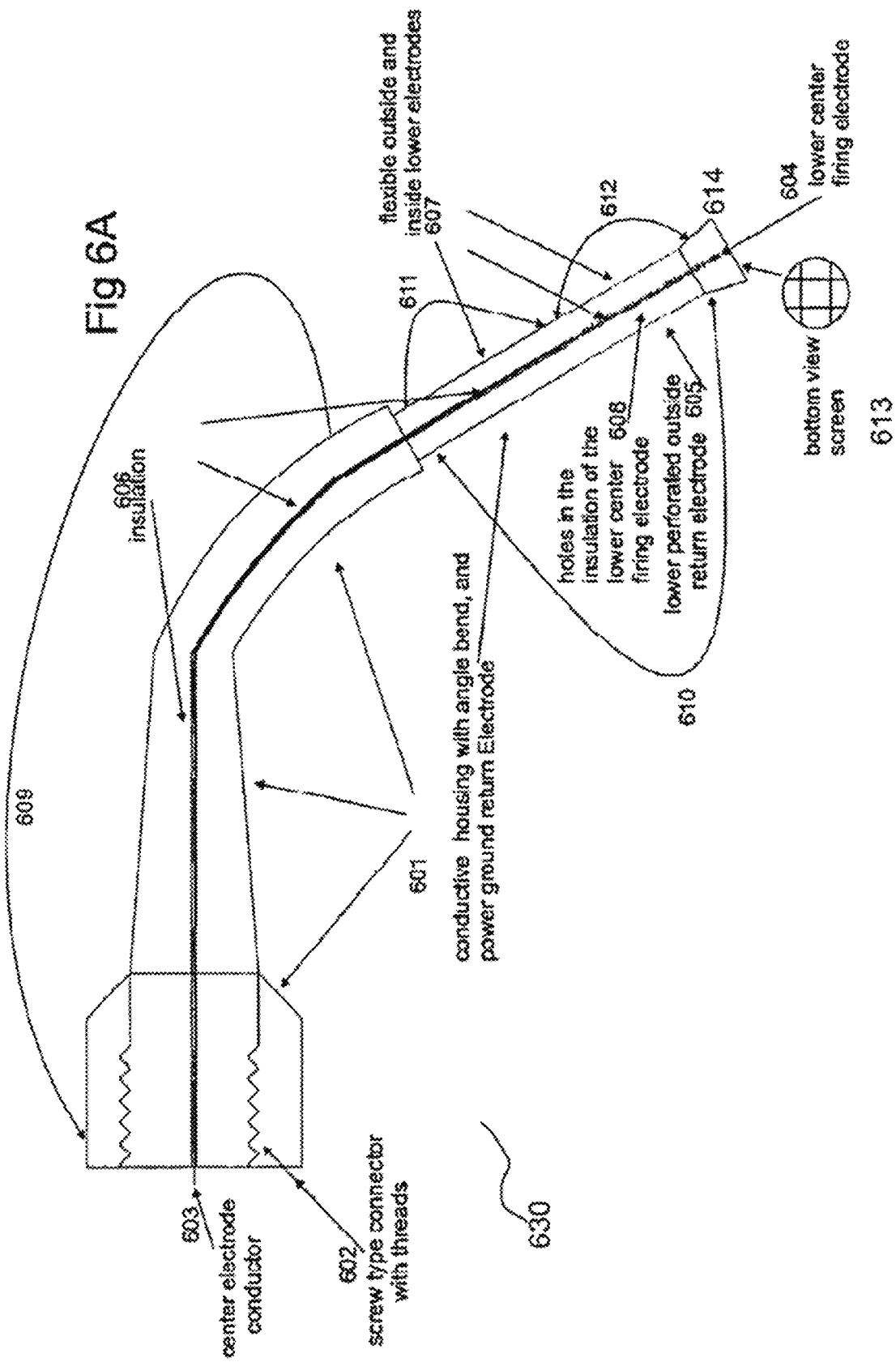

ELECTRICAL DISCHARGE IRRIGATOR APPARATUS AND METHOD

CROSS-REFERENCE TO RELATED APPLICATION

This application is a continuation of U.S. non-provisional application Ser. No. 16/351,039, filed Mar. 12, 2019, which is a continuation of U.S. non-provisional application Ser. No. 14/427,469, filed Mar. 11, 2015 which issued on Mar. 19, 2019 as U.S. Pat. No. 10,232,164, which is a National Stage application based on International Application No. PCT/US2012/070080, filed Dec. 17, 2012, published as WO 2014/042665 A1 on Mar. 20, 2014, which claims the benefit of U.S. Provisional Application No. 61/699,568, filed Sep. 11, 2012 which are incorporated herein by reference.

FIELD OF INVENTION

The present invention relates to an apparatus and method of utilizing acoustic waves created by an electrical discharge for irrigation and disinfection.

BACKGROUND OF INVENTION

Foreign bodies, such as bacteria and microbes pose a risk to dental health. These foreign bodies can invade canals and other hard to reach areas in dental structures and compromise dental health. It is the infections that are caused by the persistence of these foreign bodies that pose one of the greatest risks to the endodontic health of a patient.

Treatments to eliminate canal contents, and therefore reduce the risk of infections, range from invasive treatments, such as extraction, to the far less invasive, yet not always effective, irrigation. Irrigation involves the use of an anti-bacterial solution to flush the canals. To irrigate the canals, the solution is oscillated for irrigation at a reduced pressure. Studies have demonstrated that mechanical instruments alone cannot disinfect root canals. This is because large areas of canal walls, including apical, ribbon-shaped, and oval canals, cannot be cleaned mechanically, so microorganisms in these areas can survive. Irrigation solutions are generally required to eradicate these microorganisms and various chemicals have been used for this purpose.

Ideally, an irrigant kills bacteria, dissolves necrotic tissue, lubricates the canal, removes the smear layer, and does not irritate healthy tissue. Presently, solutions that include sodium hypochlorite (NaOCl) and ethylenemide tetra-acetic acid (EDTA) are favored by dentists. The NaOCl solution, usually at a concentration between 1%-3% is used to dissolve tissue and disinfect (remove bacteria), while EDTA removes the smear layer. During an irrigation procedure, NaOCl is used initially to dissolve tissue and disinfect and EDTA is introduced at the end of the procedure to remove the smear layer. The EDTA application is followed by another flush of NaOCl or another inert solution.

Although certainly less invasive than extraction, irrigation has its shortcomings. First, NaOCl, EDTA, and other solutions found effective in irrigation are caustic solutions, including bleaches, which when applied can badly irritate the mouth and surrounding structures. During an application, there is a risk that these solutions will perforate the apex of the canal, the end of the canal where the nerve meets the bone. If this happens, the results are so painful for a patient that the patient will end up on significant pain management, i.e., prescription pain killers, for at least two days, but sometimes, as long as two months. Second, current irrigation techniques carry a failure rate of up to 5% because often, the procedure fails to remove all the nerve tissue that is infected in the root canal system, so residual bacteria remains. Third, irrigation solutions are only effective at the time that they are applied. After a patient is treated with NaOCl and/or EDTA, the solutions are flushed out and there is no positive residual effect after the treatment is complete. Thus, any bacteria remaining in hard to reach canals will remain indefinitely and can lead to infection.

A need exists for a method and apparatus for effectively irrigating even hard to reach dental canals in a manner that produces residual benefits without causing damage and/or pain in the mouth and surrounding structures.

SUMMARY OF INVENTION

An object of the present invention is to kill foreign agents, including toxins, bacteria, and microbes, dissolve necrotic tissue, lubricate the canal, and remove the smear layer without causing damage and/or pain in the mouth and surrounding structures.

A further object of the present invention is to utilize a liquid in irrigation without the undesired side effects of bleach, or other chemical agents, while still achieving the desired anti-bacterial and other oral health benefits.

A further object of the present invention is to provide a method and apparatus for irrigation that when utilized, provides a patient with a residual antimicrobial effect after the irrigation procedure is complete.

A further object of the present invention is to provide cleaning, irrigation of the tooth canals for proper Root Canal Procedures per American Dental Association (ADA) guidelines.

A further object of the present invention is to irrigate the periodontal pocket in procedures related to both periodontal disease and peri-implantitis.

An embodiment of the present invention is a hand held irrigation device that generates a spark discharge, creating acoustical shock waves and UV radiation that irrigate dental canals and other structures, including killing foreign agents, during an irrigation treatment, and also introduce one or more of the following: UV light, hydrated electrons, OH radicals, $H_2O_2$, ozone, nanoparticles, and/or positive ions, which act to combat foreign agents even after use of the device has ceased.

An embodiment of the present invention comprises a housing, a low voltage power source, a means to convert the low voltage to a high current voltage, including but not limited to a timing circuit, means to produce a high voltage spike, including but not limited to a high voltage igniter switch, and an air gap switch, to allow the energy to discharge completely through one or more electrodes embedded in and/or external to the tip of the embodiment. An embodiment of the present invention employs capacitors to store the energy before discharge. In an embodiment of the present invention that does not utilize a spark gap, a transformer at a high impedance state delivers a high voltage spike and current to cause an acoustical shock wave.

The tip of an embodiment of the present method and apparatus utilizes electrodes comprised of biologically inert materials, including but not limited to, silver, copper, stainless steel, and/or iron, which have a toxicity to bacteria and act as anti-pathogens. The nanoparticles created by the electrodes combat the bacteria and foreign particles in the canals.

An embodiment of the present apparatus and method utilizes a spark discharge from an electrode in an embodiment of the apparatus in order to irrigate dental structures, i.e., kill foreign agents, including toxins, bacteria, viruses, and microbes, dissolve necrotic tissue, lubricate the canal, and remove the smear layer without causing damage and/or pain in the mouth and surrounding structures while providing residual resistance to these foreign agents. The utilization of the spark discharge from the electrode in an embodiment of the present apparatus creates "shock waves" in the irrigation fluid, which have a high gradient at their front, so the difference in pressure created in the irrigation fluid damages bacterial membranes and often destroys or weakens them. Because these waves needn't hit bacterial targets directly to be effective, the effects of the waves can penetrate canals and dental structures that are difficult to reach. The discharge column created utilizing an embodiment of the present method and apparatus is a source of ultra-violet (UV) radiation, which when absorbed by water molecules in the irrigating fluid produces $H_2O_2$ ozone, and OH radicals, which destroy microbes and also some organic compounds. The spark discharge of an embodiment of the invention additionally disseminates hydrated electrons, nanoparticles, and positive ions (from metal electrodes utilized in various embodiments) which continue anti-microbial and anti-bacterial action against foreign agents after the irrigation procedure has terminated.

In an embodiment of the present invention, results of utilizing a spark discharge from an electrode in an embodiment of the apparatus to eradicate pollutants, such as bacteria, can include but are not limited to, mechanically destroying bacteria and microbial cells, chemically and permanently changing the cells so they cease regular biochemical activity, irreversibly changing the genetic system of the cells. Cellular damage sustained by the pollutants includes, but is not limited to, cracking the cell walls without releasing the contents of the cells, and dispersing the cell wall and contents of the cells, damage to the DNA structure of the cells.

An embodiment of the present method utilizes a non-abrasive irrigant, including but not limited to, saline solution and/or water. Irrigants that can be used include, but are not limited to glutaraldehyde, and/or any antibiotic and/or antimicrobial solution.

An embodiment of the present invention is utilized in conjunction with the current NaOCl and EDTA protocol discussed in the Background section.

An embodiment of the present invention utilizes an ultrasonic tip that disrupts biofilm (bacteria colonies) by using ultrasonic energy to remove the biofilm, and disrupt the bacteria. In an embodiment of this invention, the ultrasonic pulse is provided in a target area at a rate of about 25-30 KHz per second to mechanically remove the biofilm, and disrupt the bacteria. Tips utilized in this application comprise an exterior and/or interior water line system that delivers water to cool the tips and to flush the periodontic pocket with water. The flushing action cleanses the area of the bacteria that the mechanical action of the tip has disrupted in the biofilm and calculus from the tooth structure.

Embodiments of the present invention are utilized in ultrasonic treatments in Piezoelectric/Magnetostrictive scalars, and/or water piks. In these embodiments, a reservoir external to the hand piece and/or in the hand piece includes electrodes that generate the spark discharge. In an embodiment of the present invention, electrodes are embedded in the tip of the device. Water and/or fluid is treated by the electrodes and is dispensed into the mouth of a patient after it is shocked.

Embodiments of the present invention are utilized in the irrigation of the periodontal pocket in connection with treatments for periodontal disease as well as peri-implantitis.

BRIEF DESCRIPTION OF DRAWINGS

FIG. 6 depicts an aspect of an embodiment of the present invention.
FIG. 6A depicts an aspect of an embodiment of the present invention.

DETAILED DESCRIPTION OF THE INVENTION

Figure 1:
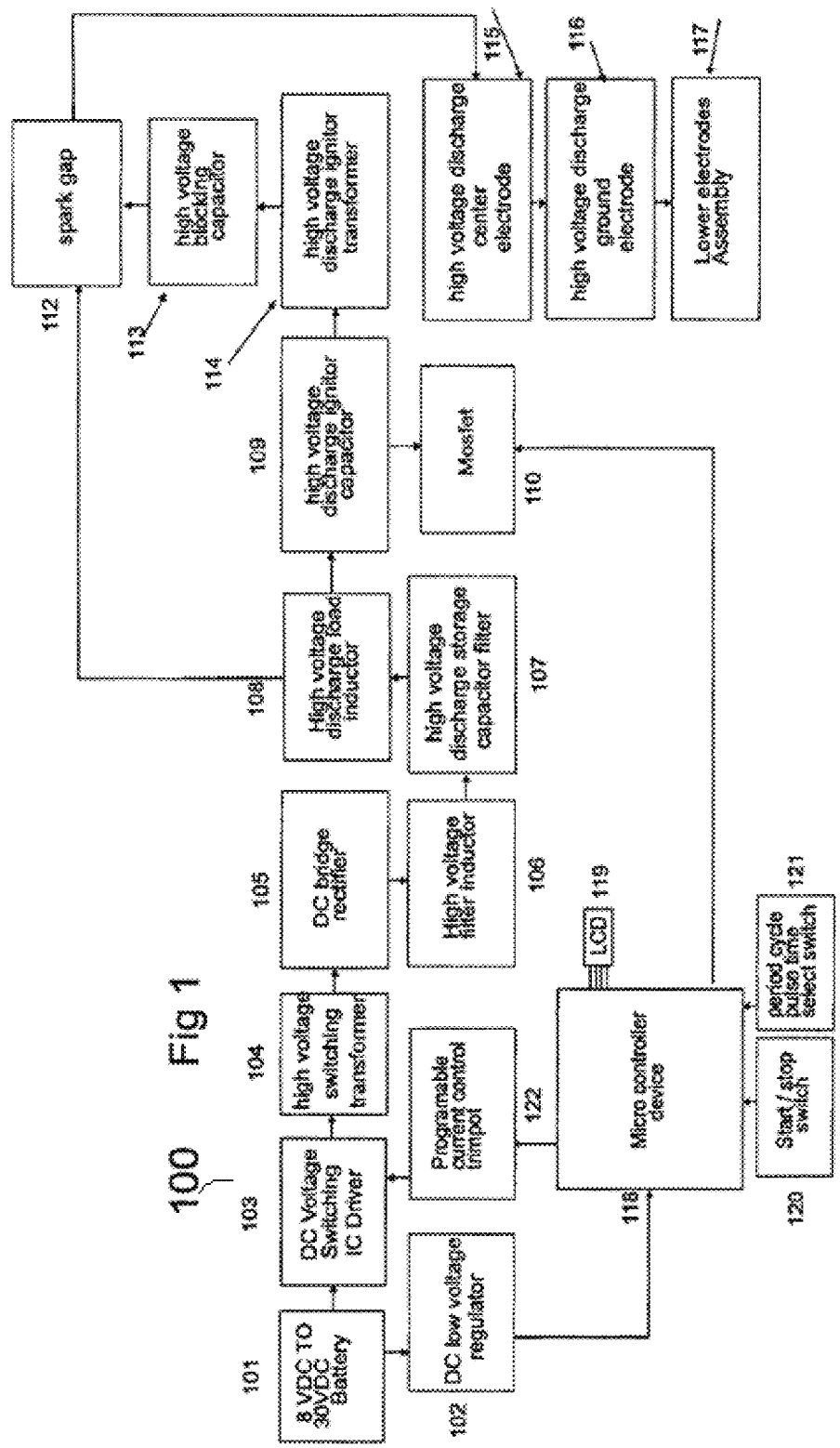
FIG. 1 depicts an aspect of embodiment of the present invention.

The apparatus and method of the present invention utilize an electric spark discharge to pulse a liquid to eradicate unwanted microbes from the liquid, such as bacteria. Embodiments of the present invention are used as irrigation systems in endodontic procedures as well as in periodontal procedures, including treatments for periodontal disease and peri-implantitis. These dental irrigation systems include, but are not limited to, an irrigation system for Piezoelectric/Magnetostrictive scalars, irrigation system for cleaning the teeth pockets and removing biofilm, a water pick irrigation system for cleaning the teeth, an irrigation system for flushing the periodontal pocket, and/or an irrigation system for surgery for disinfecting wounds. While some embodiments of the present invention pulse liquid that is external to the device directly, for example, in dental canals in endodontic uses, some embodiments of the present invention contain one or more internal reservoir(s) where the liquid and/or water used is pre-treated (pre-pulsed) before it is released into the treatment area, for example, in Piezoelectric/Magnetostrictive scalars and/or water piks.

An embodiment of the present invention utilized for endodontic procedures comprises a tube with electrodes to deliver a spark which creates the desired acoustical waves, in many of these procedures, the embodiment utilized emits electrical pulses through a tip of an embodiment of the apparatus as spark discharges. The electrical pulses agitate the liquid into which the tip is immersed and create acoustic waves, shock waves, and additional discharges that kill foreign agents, including toxins, bacteria, and microbes, dissolve necrotic tissue, lubricate the canal, and remove the smear layer while providing anti-bacterial and anti-microbial benefits both during and after treatment. Thus, an embodiment of the present invention can be utilized to irradiate bacteria and other infectious agents while providing cleaning and irrigation of the tooth canals for proper Root Canal Procedures in accordance with ADA guidelines.

An embodiment of the apparatus is used as a Piezoelectric/Magnetostrictive scalar. As discussed later in greater detail, an embodiment of the present invention utilized as a Piezoelectric/Magnetostrictive scalar utilizes an ultrasonic tip that disrupts biofilm (bacteria colonies) by using ultrasonic energy to remove the biofilm, and disrupt the bacteria. In an embodiment of this invention, the ultrasonic pulse is provided in a target area at a rate of about 25-30 KHz per second to mechanically remove the biofilm, and disrupt the bacteria. Tips utilized in this application comprise an exterior and/or interior water line system that delivers water to cool the tips and to flush the periodontic pocket with water. The flushing action cleanses the area of the bacteria that the mechanical action of the tip has disrupted in and/or fractured off the tooth structure.

In an aspect of a Piezoelectric/Magnetostrictive embodiment, the water and/or fluid that is pulsed is essentially pre-treated in one or more "holding chambers" internal to the apparatus before it passes into the water lines feeding the tips. Then, as the tip is, used it is this treated water that flushes the pockets and provides better pathogen kill, and long term protection in contrast to current methods of just using water, or a mild chemical agent and water. This current treatment has an anti microbial effect, but only while it is actually flushing the pocket. Liquids utilized in this application include, but are not limited to, a 2% glutaraldehyde solution. Pre-treating the water/liquid in internal reservoirs is also utilized in embodiments used to clean periodontic wound sites. This type of application is discussed in greater details in FIG. 10.

Returning to endodontic uses, an embodiment of the present invention is a hand held irrigation device that generates a spark discharge, creating acoustical shock waves in an irrigant and UV radiation that irrigate dental canals and other structures during an irrigation treatment, and also introduce one or more of the following: hydrated electrons, OH radicals, $H_2O_2$, ozone, nanoparticles, and/or positive ions, which act to combat foreign agents after use of the device has ceased. Further embodiments of the present invention are mounted or table top models, as opposed to hand held.

An embodiment of the hand-held version of the present apparatus, which is utilized, for example, for endodontic treatments, is comprised of a handle, which is used to grip and manipulate the apparatus, a body, where various electrical components are housed, and a tip, which contains one or more electrodes, which is inserted into liquid in the mouth of a patient in order to irrigate a selected area using acoustic waves generated by one or more circuits in the apparatus. An embodiment of the tip of the apparatus is comprised of flexible material such that it can be positioned deep within dental canals.

An embodiment of the apparatus contains a low voltage power source and the internal circuitry of the apparatus, discussed later in greater detail, converts the initial low voltage power, to high voltage power, which pulses the liquid into which the tip is immersed. The tip of an embodiment of the present method and apparatus utilizes electrodes comprised of biologically inert materials, including but not limited to, silver, copper, stainless steel, and/or iron which have a toxicity to bacteria and act as an anti-pathogen. The nanoparticles created by the electrodes combat the bacteria and other foreign particles in the canals.

In an embodiment of the present invention, because the spark discharge itself destroys foreign agents both during and after an irrigation treatment, the irrigant utilized needn't possess antiseptic or anti-bacterial qualities on its own. For example, although NaOCl and EDTA can be used in conjunction with this method, saline and water solutions are also effectively used with this method. In general, any anti-bacterial and/or anti-microbial fluids utilized in irrigation protocols are compatible with this apparatus and method In fact, the conductivity of the liquid assists in the transmission of the acoustic pulse and additional particles that irradiate the foreign agents. Thus, because water is conductive, it works well with the present method and apparatus.

In the embodiments of FIGS. 1-2 and 4-5, the power source of the apparatus is located in the handle of the apparatus and the circuitry is in the body, however, one of skill in the art will recognize that this arrangement can be altered as desired to manipulate or improve the ergonomics of the apparatus. Further embodiments of the present invention may utilize a streaming power source.

The utilization of the spark discharge from one or more electrodes in the tip of an embodiment of the present apparatus create(s) "shock waves" in the irrigation fluid which have a high gradient at their front, so the difference in pressure created in the irrigation fluid damages bacterial membranes and/or destroys them. The waves are effective in a given radius and therefore penetrate canals and dental structures that are difficult to reach and thus effectively irrigating them.

The pulsed shock waves, referred to as pulsed electrical discharges and pulsed shock discharges, damage pollutants on a cellular level. The pulses may mechanically destroy bacteria and microbial cells, chemically and permanently change the cells so they cease regular biochemical activity, and/or irreversibly change the genetic system of the cells. Cellular damage sustained by the pollutants includes, but is not limited to, cracking the cell walls without releasing the contents of the cells, and dispersing the cell wall and contents of the cells, DNA disruption.

The embodiment of the tip additionally discharges UV radiation, which when absorbed by water molecules in the irrigating fluid produces ozone, $H_2O_2$ and OH radicals, which destroy microbes and also some organic compounds. The spark discharge of an embodiment of the invention additionally disseminates hydrated electrons, nanoparticles, and positive ions (from metal electrodes utilized in various embodiments) which continue anti-microbial and anti-bacterial action against foreign agents after the irrigation procedure has terminated.

One advantage of embodiments of the present invention is that they are effective against pollutants yet are able to utilize relatively low power settings over relatively short periods of time and achieve high levels of efficiency. For example, an embodiment of the present invention eradicates foreign agents from a selected medium in 1-5 minutes at between 20 Hz, the energy in 3-20 joules. These settings are exemplary as dependent upon the use of the apparatus and the embodiment of the apparatus, the power settings and the duration of a treatment will vary.

Figure 2:
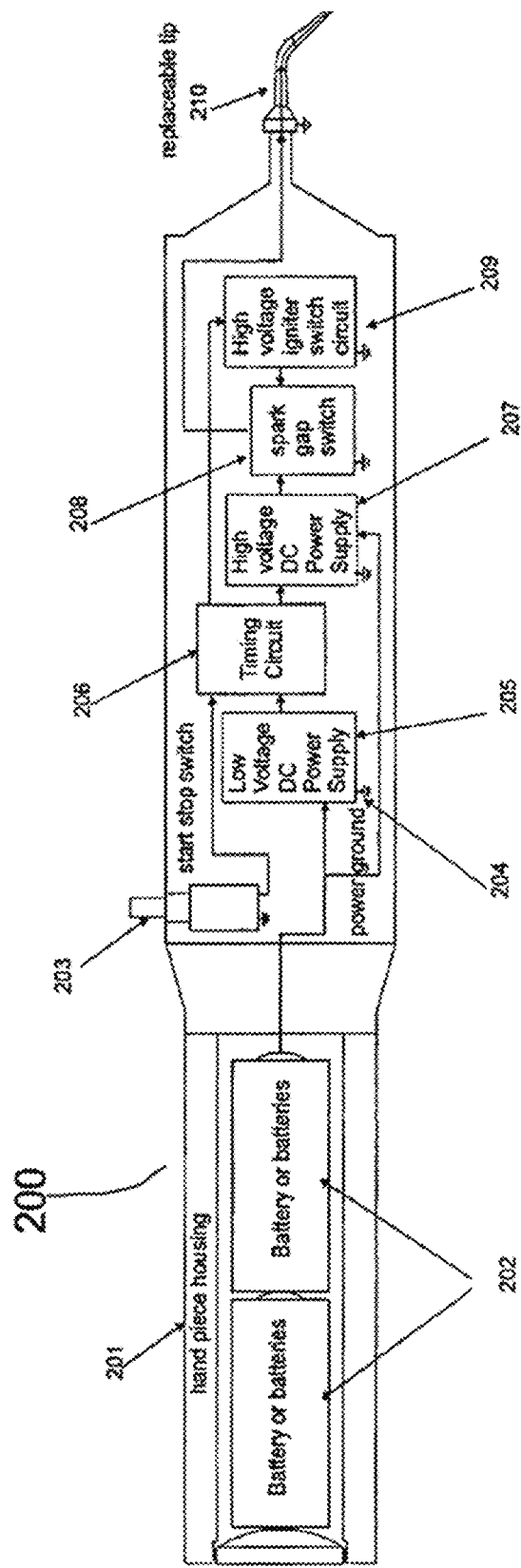
FIG. 2 depicts an aspect of an embodiment of the present invention.

FIG. 1 depicts an embodiment of the present apparatus 100. For clarity, the elements of this embodiment are depicted as black boxes. One of skill in the art will recognize the components from their descriptions. Also, later figures, such as FIG. 2, provide more detail regarding the visual appearance of the individual components.

In the embodiment of FIG. 1, the power source, the batteries 101, are contained in a hand piece housing (not pictured). The center electrode 115, the ground return electrode 116, and the lower electrodes assembly 117 are located in or on the tip, which makes contact with liquid into which a portion of the tip is submerged to create the acoustic waves therein. The remainder of the labeled elements in FIG. 1 is internal to a body portion of the apparatus. As explained later in reference to FIGS. 6-6A, the tip contains both positive and negative electrodes, however, the positions of these electrodes is interchangeable across embodiments of the present apparatus.

Referring to FIG. 1, a housing (not pictured) encompasses the electronic circuits and other fragile and electro-charged items. In some embodiments of the present invention, the housing is made of a material that does not conduct electricity as the apparatus is held in the bare or minimally protected hand of the operator. Materials used to form the housing include, but are not limited to, plastic, wood, fiberglass, metal, and/or a composite material. The utilization of a plastic housing in an embodiment of the present invention represents a savings in manufacturing costs. In further embodiments of the present invention, the housing is conductive and serves as a ground return. The housing includes an opening for easy replacement of the batteries 101 in a battery compartment (not pictured) inside the housing. The housing is also molded in a manner that allows for easy cleaning and easy replacement of the battery or batteries 101 and is ergonomically designed to be held and manipulated by an operator.

One of skill in the art will recognize that a battery or batteries 101 is only one of many power source options for this device. For example, further embodiments of the present invention utilize solar cells as power sources. In FIG. 1, the battery or batteries 101 serve as a low voltage power source that is later converted to a higher voltage by later components of this embodiment. Batteries 101 utilized in embodiments of the apparatus include but are not limited to lithium batteries, such as ion lithium batteries. In some embodiments of the present invention, lithium batteries are utilized because they have a high current and rapid charging times. Additionally, lithium ion batteries have high energy storage density for their size, which is advantageous in embodiments of the present invention because the smaller the apparatus, the easier it is for an operator to use. Additionally, lithium Ion batteries have a high energy density for their sizes, have no memory problems, can be charged quickly, and have an efficient discharge of current. One of skill in the art will recognize that lithium and lithium ion batteries although compatible with some embodiments of the present invention are only one example of a power source utilized by embodiments of the present apparatus.

A non-battery low voltage power source is used in conjunction with a further embodiment. For example, another embodiment of the present invention is a table top model that utilizes an electrical wire to connect the hand piece to the power source, and box. This embodiment utilizes a standard power cord to provide the power, including but not limited to, a 110V to 220 ac 50/60 Hz.

The battery compartment and the housing allow for the easy replacement of the battery or batteries 101. Thus, maintenance of the power source is simplified. The battery and/or batteries 101 housed in the battery compartment to power the apparatus include, but are not limited to, 0.8 vdc-30 vdcbatteries.

Coupled to the housing with the internal battery compartment is a DC low voltage regulator 102 that regulates the function of at the electronic components and integrated circuits in the embodiment of the apparatus. Coupled to the low voltage regulator 102 is a DC voltage switching integrated circuit (IC) driver 103 that drives power metal-oxide-semiconductor field-effect transistor (MOSFET) 110 and high voltage switching transformer 104 to convert the 0.8 vdc-30 vdcbattery input to a bus voltage of 300 vdc. High voltage switching transformer 104 includes, but is not limited to, a high frequency ferrite core transformer.

In this embodiment, a ferrite core transformer is utilized because it has a high frequency, is small, is very efficient, and it can handle a high current. The small size is ergonomically advantageous in hand-held embodiments of the device. The high current tolerance allows a ferrite core transformer to rapidly charge a high voltage discharge storage capacitor filter 107, such as a photo flash storage capacitor. The acoustic pulses generated in the apparatus are fast and repetitive, so the rapid charging is desirable in its operation. Further embodiments of the present invention utilize various transformers with one or more of the advantages enumerated regarding the ferrite core transformer. Further embodiments of the present invention utilize various capacitors with similar electrical properties.

In this embodiment, the converted 300 vdc voltage drives the acoustical shock wave in the liquid solution that creates the desired acoustic effect used for irrigation, which includes irrigation in endodontic procedures. Further embodiments of the present invention convert lower voltage from a power source, such as a battery, to higher voltage power ranging, for example, from 250 vdc to 500 vdc. The measure of the voltage differs in accordance with the application of the associated embodiment.

A bridge rectifier 105 is coupled to the high voltage switching transformer 104 and converts the AC output of high voltage switching transformer 104. Then, a high voltage filter inductor 106 filters out the AC ripple current for proper operation of the high voltage discharge storage capacitor filter.

In an embodiment of the present invention, a photo flash storage capacitor is used as the high voltage discharge storage capacitor filter 107 because a photo flash storage capacitor has low impedance and is capable of withstanding multiple and repetitive discharges without overheating or breaking down, i.e., incurring damage to its electrical properties. Further embodiments utilize varied high voltage energy storage capacitors and/or capacitor banks with low impedance. One of skill in the art will recognize additional capacitors beyond photo flash storage capacitors that possess these enumerated properties. Embodiments of the present invention may utilize one or more capacitors with these properties. When multiple capacitors are utilized, they may be of the same or of different types.

The high voltage discharge storage capacitor filter 107 is coupled to a high discharge load inductor 108 so that the high discharge load inductor 108 saturates under high discharge current from a low impedance to a high impedance, thus isolating the switching power portion of the circuit.

After this isolation is achieved, a high voltage discharge igniter capacitor 109 discharges all the energy into a high voltage discharge igniter transformer 114, causing a very a high voltage pulse, which is utilized to agitate liquid and create the acoustical waves utilized for irrigation and disinfecting. In this embodiment, a MOSFET 110 discharges voltage discharge igniter capacitor 109 into the high voltage discharge igniter transformer 114. Further embodiments of the present apparatus utilize additional transistors, including but not limited to, a silicon-controlled rectifier (SCR) transistor.

The activity of the MOSFET 110 is controlled by a micro controller device 118. In addition to the activity of the MOSFET 110, the micro controller 118 controls functions within this embodiment of the apparatus, including but not limited to, the period time and the cycle time (Hz) and the current of the power portion of the circuit. The pulse time is a function of the stored energy, which in this embodiment is denoted in micro seconds. By utilizing the micro controller device 118 to set the current, battery power can be conserved within this embodiment.

Once the energy is discharged by the high voltage discharge igniter capacitor 109, the high voltage discharge igniter transformer 114 creates a high voltage pulse. The high voltage pulse breaks down the air spark gap and liquid solution so that the high voltage discharge igniter capacitor 109 can discharge all its energy. The high voltage discharge igniter transformer 114 is isolated using a high voltage blocking capacitor 113. As aforementioned, the high voltage discharge igniter transformer 114 is a low impendence device and would be damaged by the high current that is discharged and stored in the high voltage discharge storage filter 107.

In this embodiment, a spark gap 112 serves as a high voltage switch. The spark gap 112 isolates the high voltage power supply and the energy stored in the high voltage discharge storage filter 107. Because the liquid solution into which the tip of the apparatus is immersed is somewhat conductive, without the spark gap 112, the charge conducted in the liquid would load the power portion of the circuit. The spark gap 112 allows the high voltage power portion to completely charge to obtain a high current discharge. The high voltage pulses created by the high voltage discharge igniter transformer 114 break down the air spark gap and liquid solution, allowing the high voltage discharge igniter capacitor 109 to discharge all its energy, making this spark gap 112 into a high voltage switch.

The tip of the apparatus, which is optionally replaceable, is discussed in greater detail in reference to FIGS. 6-6A. However, components of this tip are depicted in FIG. 1.

Referring to FIG. 1, the tip includes center electrode 115, which in an embodiment of the present invention is a high voltage discharge positive electrode, a ground return electrode 116, which in an embodiment of the present invention is a high voltage discharge negative electrode, and a lower electrode assembly 117, which comprises the firing chamber (not pictured). The center electrode 115, so-called due to its location in some embodiments of the tip, is embedded in the tip and the ground return electrode 116 is located on the outside of the tip. At the lower portion of the tip, holes in both a conductive housing (not pictured) that surrounds electrodes in the tip and in the insulation (not pictured) within the tip, allow liquid solutions to enter into the firing chamber (not pictured). The chamber includes the lower electrode assembly 117. This is where the discharge takes place. The lower electrode assembly 117 in the tip is placed in liquid in order to agitate the liquid and create the acoustic waves utilized in the irrigation of targeted areas.

In one embodiment of the present invention, the center electrode 115 is a negative electrode and the ground return electrode 116 is a positive electrode. The charges of the electrodes vary provided that there is a center electrode and a return electrode with different charges to create pulses. The apparatus creates the electrical discharge utilizing a center electrode 115, and a ground return electrode 116, which will be discussed in more detail in reference to FIG. 6.

Coupled to the aforementioned micro controller device 118 is a liquid crystal display (LCD) 119 to aid the user in accurately utilizing the apparatus. As this embodiment is programmable, the LCD 119 displays the selected settings to the user.

Further embodiments of the present invention utilize varying displays and some do not utilize a display, as the display, although user-friendly, can affect the cost of the apparatus. A start/stop switch 120 coupled to the micro controller 118 initiates and deactivates the apparatus. A second switch, a period cycle pulse time select switch 121, allows the user to select the period time and cycle time. In another embodiment of the present invention, the LCD display 119, or an alternative display, is integrated with a touchscreen with start/stop and/or selection controls which include the same functionality as the start/stop switch 120 and the period cycle pulse time select switch 121. Also coupled to the micro controller device 118 is a programmable current control trimpot 122, which is used to interface with the micro controller device 118 and the DC voltage switching IC driver 103.

FIG. 2 is another embodiment of the apparatus 200. FIG. 2 is designed to reflect the shape and ergonomic design of the apparatus. This embodiment is hand-held and therefore, the hand piece housing 201 is easily gripped and the embodiment of the apparatus easily manipulated by a user. On the end of the apparatus 200 is a replaceable tip 210, an embodiment of which is discussed further in reference to FIG. 6.

Like the embodiment of FIG. 1, the hand piece housing 201 of FIG. 2 is molded of a non-conductive material, such as plastic, and the hand piece housing 201 is also molded as such that allows for easy cleaning and easy replacement of the batteries 202 within. In another embodiment of the present invention, the housing is conductive and serves as a ground return. Embodiments that utilize plastic, non-conductive housings may reduce manufacturing costs.

The two compartments for the batteries 202 in this embodiment are shown as a non-limiting example. Depending upon the batteries selected, the number used to achieve the acoustical pulse generated by the apparatus varies. Batteries 202 utilized in this embodiment include but are not limited to 0.8 vdc-30 vdc batteries. The low voltage of the batteries 202 is later magnified by additional components in the embodiment, as in the embodiment of FIG. 1, to drive the acoustical shock wave in the liquid solution that creates the acoustic effect used, for example, in endodontic irrigation.

The batteries 202 charge a low voltage DC power supply 205 with a power ground 204. A timing circuit 206 takes input from the low voltage DC power supply 205 while also taking input from a start/stop switch 203. The operation of the start/stop switch 203 by a user controls whether the apparatus is operational. This timing circuit 206 powers a high voltage igniter switch circuit 209. In this embodiment of the apparatus 200, the start/stop switch 203 controls the operation of the embodiment.

In this embodiment 200, the high voltage igniter switch circuit 209 is coupled to spark gap switch 208. Also coupled to the spark gap switch 208 is a high voltage DC power supply 207. The low voltage DC power supply 205, inputs to the timing circuit 206, which inputs to a high voltage DC power supply 207.

Figure 3:
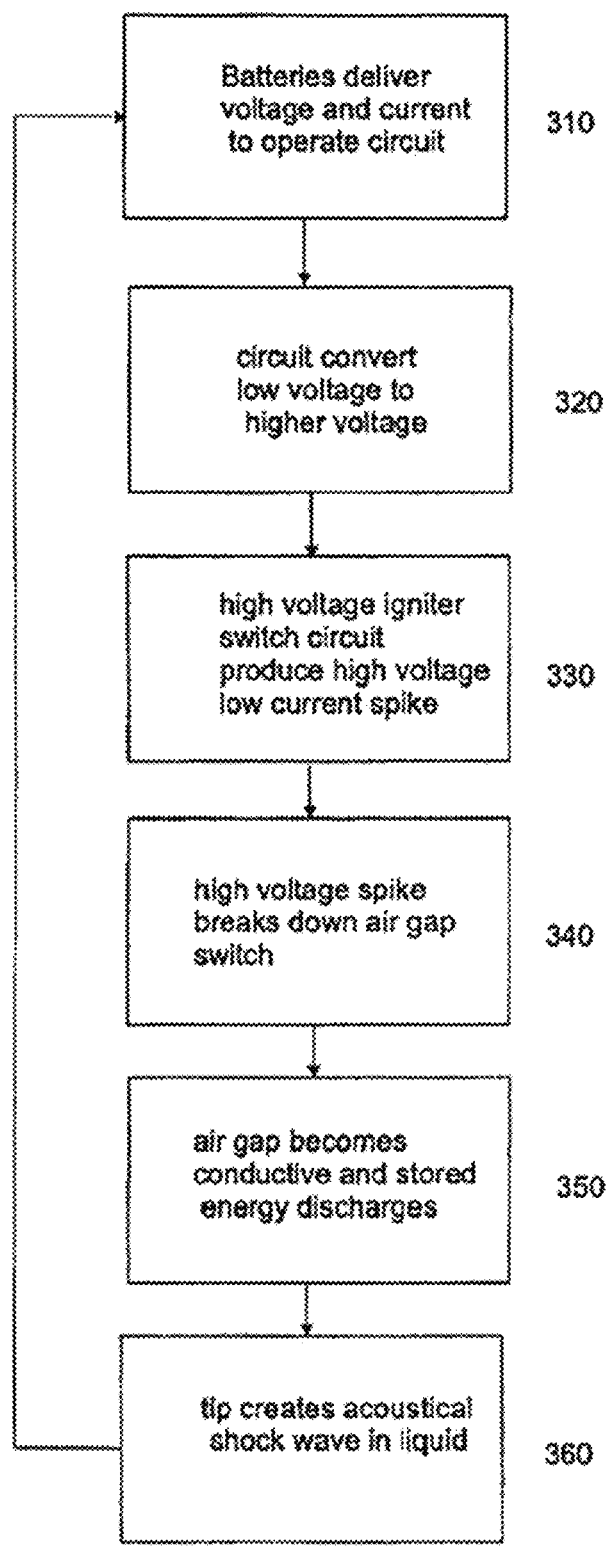
FIG. 3 depicts a workflow of an embodiment of the present invention.

FIG. 3 is a general workflow 300 of an aspect of the present invention. Throughout FIG. 3, references are made to the elements of FIG. 2 for clarity. However, FIG. 2 is only one embodiment of the apparatus. The workflow 300 is applicable across further embodiments of the apparatus.

Referring to FIG. 3, the battery or batteries 202 deliver the voltage and current to operate the circuit (S310). The low voltage dc power supply 205, which in FIG. 2 is small enough to fit in a hand held device, and the timing circuit 206, convert the low voltage to a high current/voltage (S320). The high voltage igniter switch circuit 209 produces a very sharp high voltage spike that is low in current (S330). The high voltage spike breaks down the air gap switch 208 (S340). When the spark bridges the air gap, the gap becomes conductive and it allows all the stored energy to discharge completely (S350). In various embodiments of the present apparatus, this energy is stored in capacitors, like the high voltage capacitor 109 in FIG. 1. Returning to FIGS. 2 and 3, when the stored energy discharges, the tip 210 of the apparatus is in the liquid solution and the energy travelling through the tip 210 creates an acoustical shock wave in the liquid (S360). Once a wave is created, the process repeats as the batteries 202 continue to deliver voltage to the circuit (S310).

In an embodiment of the present invention, the spark discharge achieved in FIG. 3 delivers more than just an acoustical wave to combat foreign agents, such as bacteria. The spark discharge at (S350) delivers the aforementioned acoustical shock waves, UV radiation, hydrated electrons, OH radicals, $H_2O_2$, nanoparticles, and positive ions (of embodiments of the present invention that utilize metal electrodes in the tip, discussed later in FIG. 6).

The positive electrical discharges created by the electrodes in the tip of an embodiment of the present apparatus create shock waves that are high pressure and therefore, damage the bacterial membranes due to the difference in pressure. The destroying effect on bacteria due to this pressure difference is realized more intensely with faster discharges and/or for acoustic waves on destroyed cells.

In an embodiment of the present invention, shock wave forces the irrigant through the small lateral canals at a pressure that achieves absolute irrigation of main canals coupled with irrigation of small and tiny lateral canals, including those that are oddly shaped. By utilizing an embodiment of the present invention, If a lateral comes off of a tooth, the tip can be positioned such that the discharge that is next to the tooth and will drive the irrigant directly into the lateral. In an embodiment of the present invention, the electrode in the tip, discussed further in FIG. 6, is small so that it can go down the canal and/or be placed in close proximity.

Depending upon the positioning of the tip, the method can result in the discharge of the tip partially into the air. This discharge additionally assists in the destruction of foreign agents as it serves to energize electrons, which initiate plasma chemical reactions that produce free radicals and ions which ultimately destroy foreign agents.

In addition to OH and $H_2O_2$, other products of this electrical discharge include, but are not limited to, $H^*$, $O^*$, and $O_3$ (ozone), which together with OH and $H_2O_2$ act as oxidizing agents. The electric fields of these discharges are lethal to several kinds of microorganisms. Additionally, $H_2O_2$ and $O_3$ dissociate into free radicals and these free radicals oxidize organic components. $OH^*$ also oxidizes organic components. These particles oxidize organic components both above and below the surface of the irrigant.

The UV radiation also oxidizes organic compounds in the irrigant. Thus, combining the shock wave with these oxidizing agents serves to sterilize the irrigant.

After the OH radicals, the $H_2O_2$, and the hydrated electrons have dissipated, i.e., after no more than several days, the nanoparticles and positive ions of metal, which are produced by the erosion of the electrodes, continue to provide anti-bacterial benefits. One manner in which the nanoparticles destroy bacteria is by penetrating the bacteria and emitting toxic ions. When nanoparticles are in close proximity to bacteria, directed streams of toxic ions appear, which produce a bactericidal effect. Thus, this cooperative residual bactericidal effect is accomplished at least in part by the actions of nanoparticles and positive ions emitting them. The residual effects of the nanoparticles and positive ions of metal are realized for a duration including but not limited to several months.

Embodiments of the present invention can be used both in concert with and without the NaOCl and EDTA protocol to remove all of the nerve and infected materials, clean the smear layer, and kill bacteria or pathogens. When used in conjunction with the NaOCl and EDTA protocol, this apparatus and method would kill remaining bacteria and pathogens that remain after the protocol and provide residual effects that the protocol does not provide. When used without the protocol, the apparatus and method could provide the listed functionality without introducing a toxic substance into the body. Irrigants that can be used include, but are not limited to saline solution, glutaraldehyde, and/or any antibiotic and/or anti-microbial solution.

Figure 5:
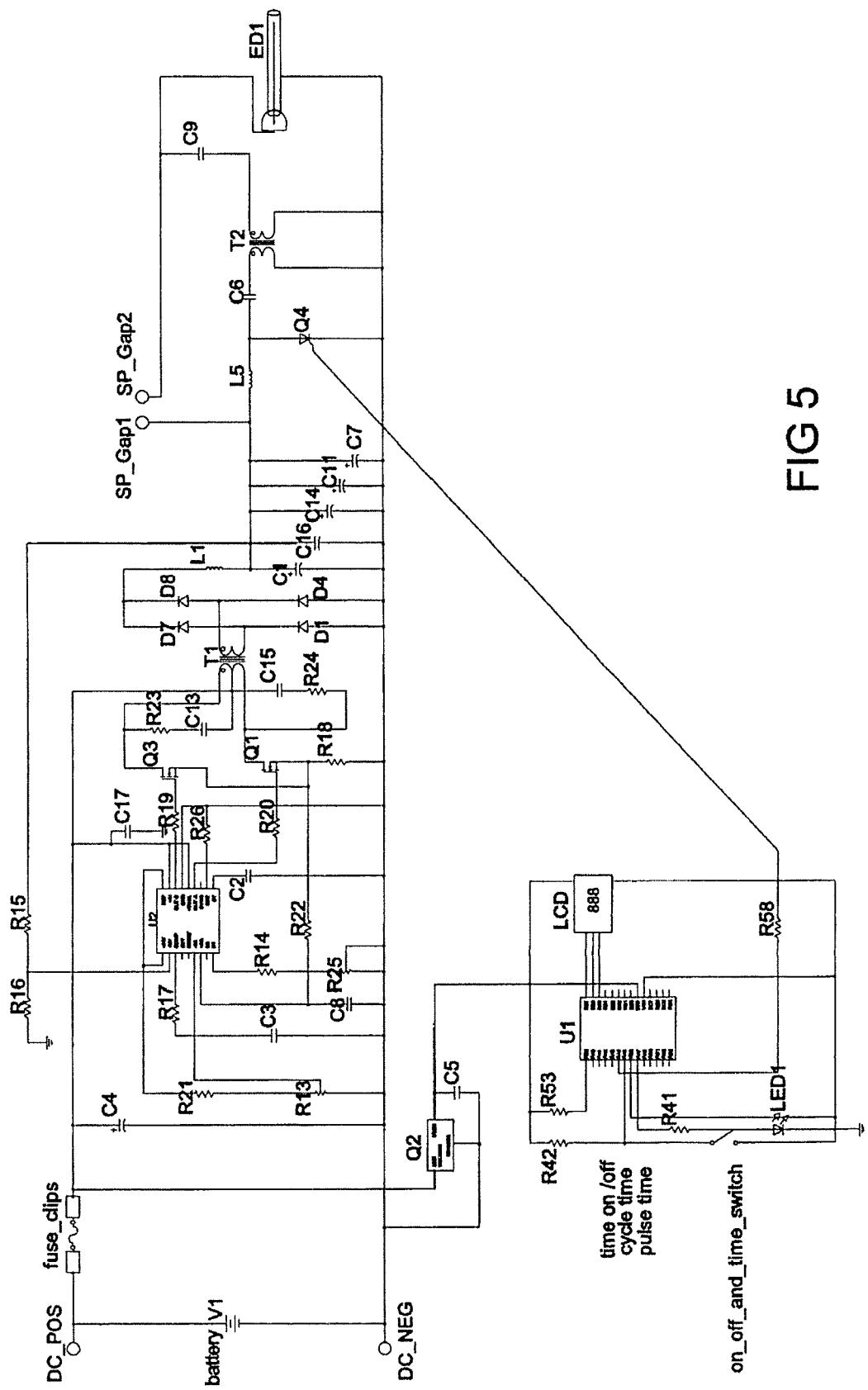
FIG. 5 depicts an aspect of an embodiment of the present invention.

FIG. 5 depicts an embodiment of the circuitry utilized in an embodiment of the present apparatus. This apparatus practices the workflow 300 of FIG. 3. The electrical elements of FIG. 5 are enclosed in a non-conductive housing (not pictured). The circuit details provided in FIG. 5 are an example of a possible configuration of circuit components utilized to practice the method disclosed. One of skill in the art will recognize that certain components can be substituted and still create an irrigating acoustic wave. For example, FIG. 5 features seventeen capacitors C1-C17, which is only one example of how capacitors can be configured in the circuitry of the present apparatus.

The functions of the apparatus in FIG. 5 are programmable by utilizing a micro chip controller U1. The micro chip controller U1 controls all timing functions, including but not limited to period time and cycle time (Hz). The pulse time is a function of the stored energy, which is measured in micro seconds.

The embodiment of FIG. 5 is powered by a lithium battery V1. The lithium battery V1 is a low voltage battery with a voltage range of 0.8 vdc-30 vdc. Further embodiments of the present apparatus employ additional power sources with voltages within this range. As discussed in reference to FIGS. 1-2, in this embodiment, this low voltage power source is later converted to a high voltage in order to create the acoustical waves that agitate liquid through the tip (not pictured) of the apparatus and irrigate dental structures in the mouth of a patient. A safety fuse F1 is additionally incorporated in this embodiment. A filter capacitor C4 is used to eliminate any electrical noise that may be generated by the switching power supply or other IC's in the embodiment. The switching power supply U2 converts the low battery voltage to a high bus voltage, which includes but is not limited to a range of 250 vdc to 500 vdc.

As seen in FIG. 5, this switching power supply U2 utilizes supporting passive and active components to set up all the levels and references. Included in these components are the 5 volts references, resistors R13, R21, which are tied to the switching power supply U2. Meanwhile, resistors R15 and R16 form a voltage divider feedback loop and are tied to the high voltage bus output. Additional resistors R19 and R20 limit the current to the gates of the MOSFETs Q1, Q3 and the IC maximum current drive output. The MOSFETs switch the high frequency transformer together with switching power supply U2 and drive them to switch on and off at a predefined frequency. Resistor R18 works as a current sensing resistor and implements electrical resistance in the circuit. Meanwhile, resistor R22 and capacitor C8 act as a buffer filter to eliminate spikes caused by switching the inductive load.

FIG. 5 utilizes a high frequency ferrite transformer T1, including but not limited to a ferrite core transformer. The high frequency transformer T1 includes MOSFET pins 1 and 3, so-called because they are tied to the MOSFETs Q1, Q3. MOSFET pin 2 is tied to the power supply, in this embodiment, a 0.8 vdc-30 vdc battery supply. The AC output pins 4, 5, of the high frequency transformer T1 feed diodes D1,D4,D7 and D8, which are set up as a full wave bridge rectifier, converting the rectified AC to DC. Resistor R23 and capacitor C13 acts as an RC snubber as does resistor R24 and capacitor C1; RC snubbers work like filters and keep spikes and radio frequency interference (RFI) noise to a minimum.

In the present embodiment, Inductor L1, together with capacitors C1, C16, C14, and C11 filter and store the energy that will be discharged at a high current rate. Specifically, Inductor L1 saturates when capacitors C1, C16, C14 and C11 are discharged.

The high voltage igniter portion of the circuit is comprised of inductor L5, MOSFET Q4, capacitor C6, and transformer T2. Capacitor C9 acts as a blocking capacitor and prevents the high discharge capacitor stored current from damaging transformer T2. As in the embodiment in FIGS. 1 and 2, an air gap SP_Gap1-SP_GAP2 is used as a switch, which loads as the capacitors C1, C16, C14, C11 are charged. The bus voltage is sufficient to cause break down of the liquid solution which is somewhat conductive. Therefore, the capacitor C9 protects the transformer T2 from being loaded down.

Figure 4:
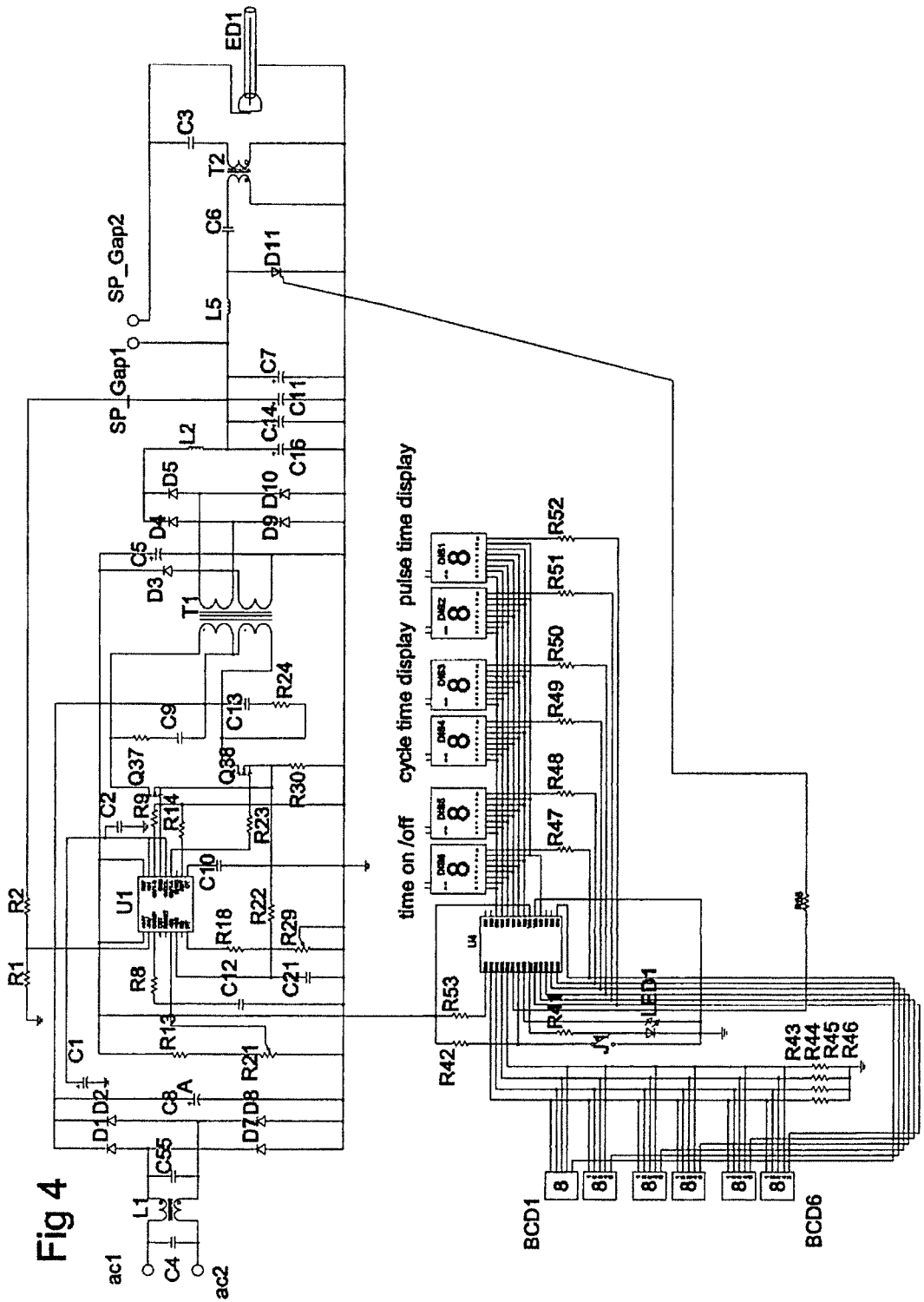
FIG. 4 depicts an aspect of an embodiment of the present invention.

FIG. 5 depicts the circuitry utilized in an embodiment of the present apparatus. The circuitry is similar to FIG. 4, but the apparatus utilizes a different control for user input. Both the embodiment of FIG. 4 and the embodiment of FIG. 5 are programmable by utilizing a micro chip controller U1. In FIG. 4, the user adjusts settings by utilizing user BCD switches BCD1-BCD6 to set the period time and cycle time. These settings are obtained by micro chip controller U1. Light-emitting diode (LED) displays DIS1-DIS6 display the countdown timer, displays DIS5-DIS6, the cycle time, displays DIS3-DIS4, and the pulse time, displays DIS1-DIS2, to a user.

FIG. 5 utilizes an LCD display LCD1 to display the countdown timer, cycle time, and pulse time to a user.

Figure 5A:
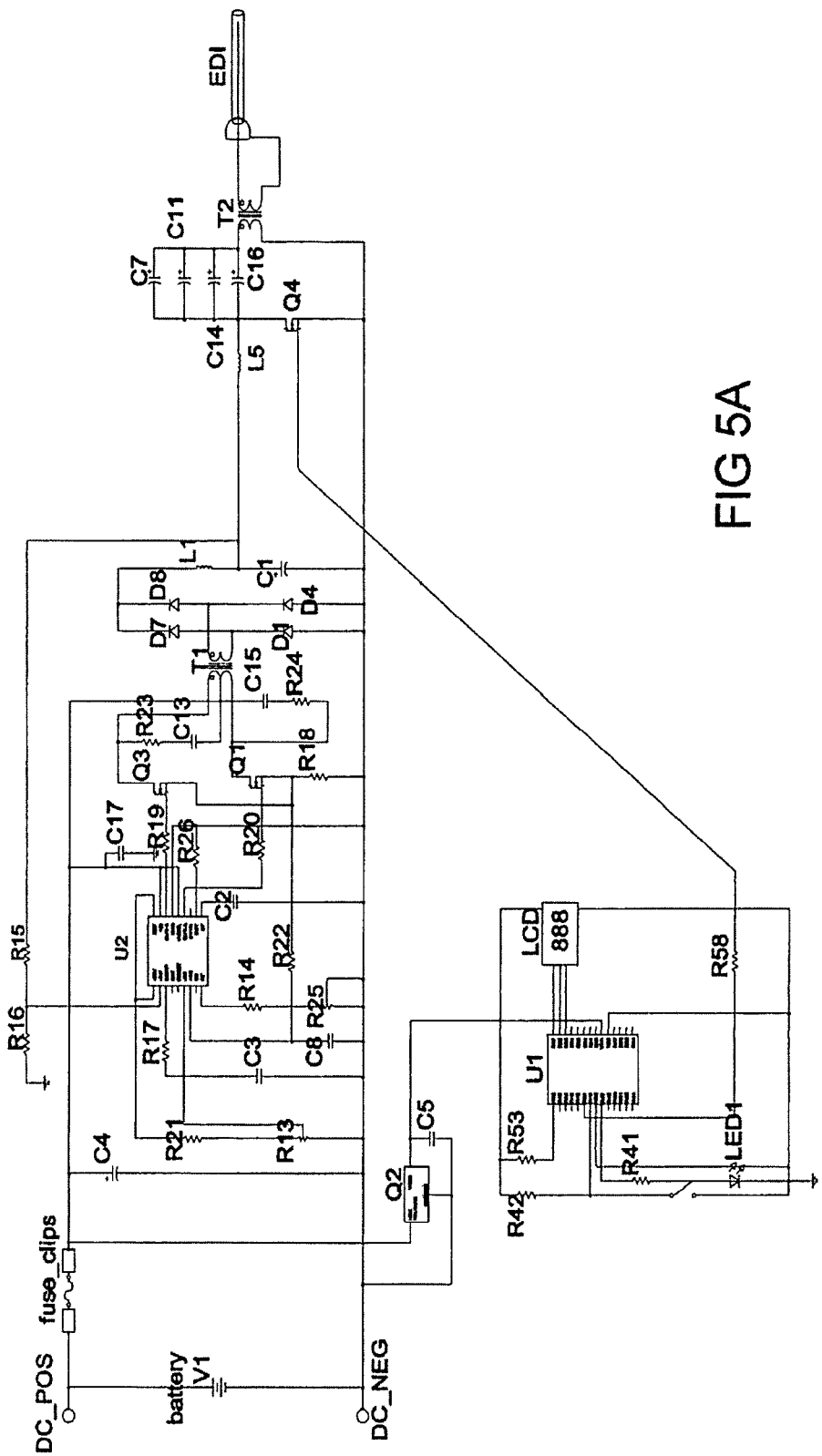
FIG. 5A depicts an aspect of an embodiment of the present invention.

FIG. 5A also depicts circuitry utilized by an aspect of an embodiment of the apparatus. In the embodiment of the apparatus that utilizes the circuitry of FIG. 5A, power is delivered to the tip (not pictured) differently. This embodiment does not utilize a spark gap to create an acoustic wave.

Referring to FIG. 5A, voltage/current travels to inductor L5 and to one or more capacitors C7, C11, C14, C16, including but not limited to, one or more photo discharge capacitors. The four capacitors utilized in FIG. 5A are depicted as an example as additional embodiments utilize different numbers of capacitors as needed depending upon the use, among other factors. Once charged, capacitors C7, C11, C14, C16 discharge at the primary of transformer T2.

In this embodiment, transformer T2 delivers a high voltage spike and current to cause an acoustical shock wave. Transformer T2 is robust as it delivers both a high voltage spike and enough current to cause the acoustical shock wave. Transformer T2 is rendered robust by a thick wire and its configuration. Not only is the wire thick, the secondary of transformer T2 is isolated from the circuit and connected directly to electrodes in the tip (not pictured).

Before the voltage/current flows through inductor L5 and charges capacitors C7, C16, C11 and C14, MOSFET Q4 gets an instruction from micro chip controller U1. The micro chip controller U1 applies voltage, including but not limited to, 5 volts, to the gate of the MOSFET Q4, so that it conducts the voltage/current. The MOSFET Q4 then turns and it discharges all the stored energy from capacitors C7, C16, C11 and C14 into transformer T2, which causes inductor L5 to momentary saturate. Transformer T2, now at a high impedance state, delivers a high voltage spike and current to cause an acoustical shock wave.

An embodiment of the tip 600 of an embodiment of the apparatus is shown in FIG. 6. The tip 600 appears as an integrated unit, but is separated into components to understand its functionality. During use, the end of the tip 600 is inserted in the mouth of a patient and in some applications, such as cleaning fissures, it may be embedded in a specific tooth that is being irrigated. The tip 600 connects to the body of the apparatus with a connector 602 that is integrated into the tip design. In the embodiment of FIG. 6, the connector 602 is a screw-type connector with threading. The receptors of the threading are located on the body of the apparatus (not pictured).

Like the hand held portion discussed in earlier figures, the tip 600 is comprised of a housing 601. This housing 601 on the tip 600 is comprised of a conductive material, including but not limited to, metal, such as stainless steel. This housing 601 is conductive because it doubles as a ground return electrode. The housing 601 is shaped with a bend that is utilized to manipulate the tip into the mouth of a patient and into the dental structure, such as the tooth, that the user of the apparatus desires to irrigate.

Although a continuous housing 601, the upper portion of the housing 609, and the lower portion of the housing 610 have differing characteristics. To protect the internal elements, in an embodiment of the present invention, the upper portion of the housing 609 is thick and rigid. The lower portion of the housing 610 is comprised of a material that is both conductive and flexible, such as a flexible stainless steel tube. The lower portion of the housing 610 is comprised of a first portion 611 and a second portion 612. The first portion 611 is solid while the second lower portion 612 is porous. The porous second lower portion 612 allows an electrical discharge to occur in the lower part of the tip 600 and permeate the tip into the liquid.

Internal to the housing 601, is a center electrode conductor 603, which conducts the charge through the tip 600. This center electrode conductor 603 is insulated using a layer of insulation 606 throughout the length of the tip 600 and the center electrode conductor 603. A porous portion of insulation 608 surrounds the lower center firing electrode 604.

In an embodiment of the present invention, the lower center firing electrode 604 is the center electrode 115 referenced in FIG. 1. In an embodiment of the invention, the lower perforated return electrode 605 is the ground return electrode 116 referenced in FIG. 1, and the insulation 606 and the perforated return electrode 605 comprise the a lower electrode assembly 117 and firing chamber referenced in FIG. 1.

In embodiments of the present invention, the center firing electrode 604 is either a positive or a negative electrode, and the lower perforated return electrode 605 is either a positive or a negative electrode. In each embodiment, the center firing electrode 604 has a charge that opposes that of the lower perforated return electrode 605. One of skill in the art will recognize that a center electrode and a ground electrode, regardless of charge, may be adapted to create the desirable electrical events within the tip of embodiments of the present invention.

Returning to FIG. 6, the lower center firing electrode 604 is embedded in the tip 600, while the lower perforated return electrode 605 is located in the outside of the tip 600. The porous second lower portion 612 of the tip 600, the porous portion of insulation 608 surrounding the lower center firing electrode 604, and the perforated return electrode 605 allow liquid solution to make contact with the lower center firing electrode 604. The conductive liquid bridges the connection between the lower perforated return electrode 605 and the lower center firing electrode 604 so that the tip can deliver acoustic waves into the area targeted by the tip. The lower center firing electrode 604 transfers the energy into the liquid solution that causes the acoustical shock wave, while the holes in the lower perforated outside return electrode 605 allow the acoustical shock wave to penetrate into the liquid solution. Flexible outside and inside lower electrodes 607 assist in positioning the tip 600 to deliver the acoustic waves to a targeted area. Specifically, the flexible outside and inside lower electrodes 607 allow the tip 600 to be worked into the tooth or the root canal for performing the irrigation of the root canal and laterals.

In an embodiment of the present invention, the electrodes utilized include silver. Water treated with silver electrodes has the highest bactericidal activity because ions of silver have the highest toxicity to bacteria; it is an anti-pathogen. Thus, the nanoparticles created by the silver electrodes also combat the bacteria and foreign particles in the canals. Further embodiments of the present invention utilize electrodes comprised from additional materials that are biologically inert ones. Materials used to comprise the electrodes include but are not limited to silver, copper, stainless steel, and/or iron.

As aforementioned, the tip of an embodiment of the apparatus may be removable and may be switched out with different tips that are more suited for different applications. In embodiments where the tips are not removable, the tip design may vary to maximize efficacy across varying uses. FIG. 6A shows an embodiment of a tip that is designed to fire at the surface. The tip 601 has a larger opening at the bottom 614 to fire onto a greater surface.

As in the embodiment of FIG. 6 the tip 630 in FIG. 6A, utilizes a connector 602, including but not limited to a screw-type connector with threading. Further embodiments of this tip 630 and the tip 600 of FIG. 6 may utilize additional fasteners. Returning to FIG. 6A, when threading serves as the connector 602, the receptors of the threading are located on the body of the apparatus (not pictured).

Tip 630 is comprised of a housing 601, which is comprised of a conductive material, including but not limited to, metal, such as stainless steel which doubles as a ground return electrode and is shaped with a bend that is utilized to manipulate the tip into the mouth of a patient. The upper portion of the housing 609 is thick and rigid. The lower portion of the housing 610 is comprised of a material that is both conductive and flexible, such as a flexible stainless steel tube. The lower portion of the housing 610 is comprised of a first portion 611 and a second portion 612. The first portion 611 is solid while the second lower portion 612 is porous. The porous second lower portion 612 allows an electrical discharge to occur in the lower part of the tip 630 and permeate the tip into the liquid.

The tip 630 features at least two electrodes, a center electrode and a ground electrode. The electrodes may be comprised of a metal and/or other conductive materials with anti-bacterial properties, including but not limited to, silver.

Internal to the housing 601, is a center electrode conductor 603, which conducts the charge through the tip 630 and is insulated using a layer of insulation 606 throughout the length of the tip 630 and the center electrode conductor 603. A porous portion of insulation 608 surrounds the lower center firing electrode 604. The lower center firing electrode 604 is embedded in the tip 630, while the lower perforated return electrode 605 is located in the outside of the tip 630. The porous second lower portion 612 of the tip 630, the porous portion of insulation 608 surrounding the lower center firing electrode 604, and the perforated return electrode 605 allow liquid solution to make contact with the lower center firing electrode 604. The conductive liquid bridges the connection between the lower perforated return electrode 605 and the lower center firing electrode 604 so that the tip can deliver acoustic waves into the area targeted by the tip. The lower center firing 4 electrode 604 transfers the energy into the liquid solution that causes the acoustical shock wave, while the holes in the lower perforated outside return electrode 605 allow the acoustical shock wave to penetrate into the liquid solution. Flexible outside and inside lower electrodes 607 assist in positioning the tip 630 to deliver the acoustic waves to a targeted area. Specifically, the flexible outside and inside lower electrodes 607 allow the tip 630 to be worked into the tooth or the root canal for performing the irrigation of the root canal and laterals.

The end 614 of the tip 630 is fitted with a screen 613. The screen 613 has a slight angle with a bigger opening at the bottom. Tip 630 is utilized in one aspect to fire at the surface. Thus, the greater surface area allows greater and more concentrated dispersion of firing discharges, including but not limited to UV, ozone, shock wave, radicals, and ions pulse at the surface. The screen 613 is part of the ground return and prevents an electrical charge from passing the end of the tip and having an adverse effect on a patient being treated.

As aforementioned, an embodiment of the present invention can be used to create an irrigation system for Piezo-electric/Magnetostrictive scalars, like a water pik-type device with additional bactericidal benefits. In this application, water is pretreated before being expelled into the mouth of a patient.

Figure 7:
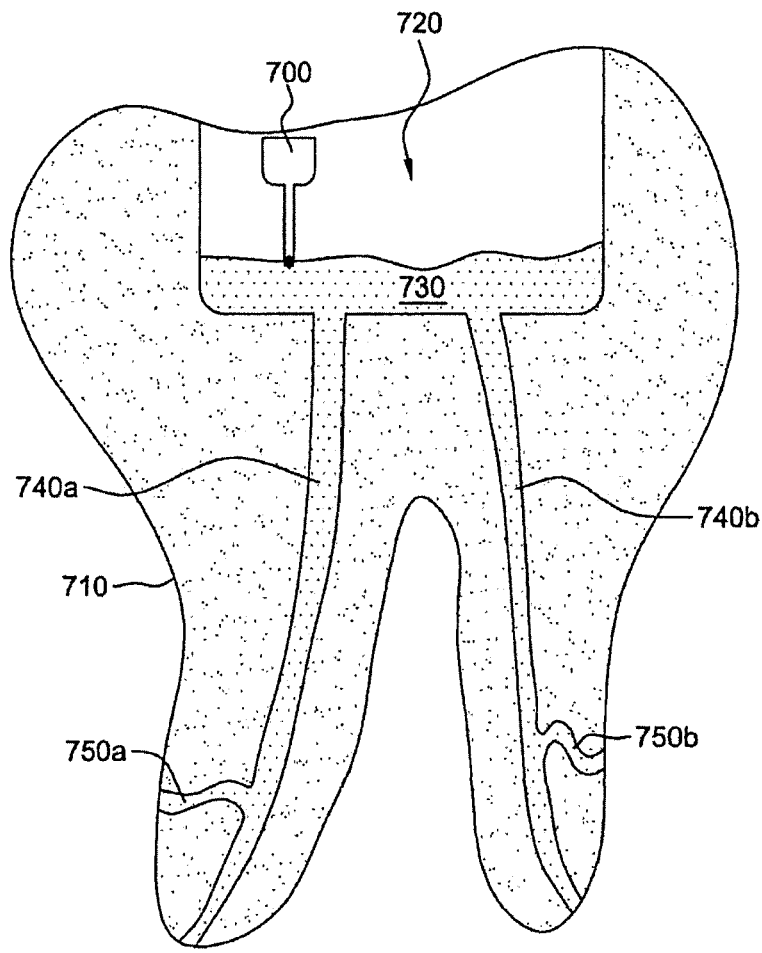
FIG. 7 depicts an aspect of an embodiment of the present invention.
Figure 8:
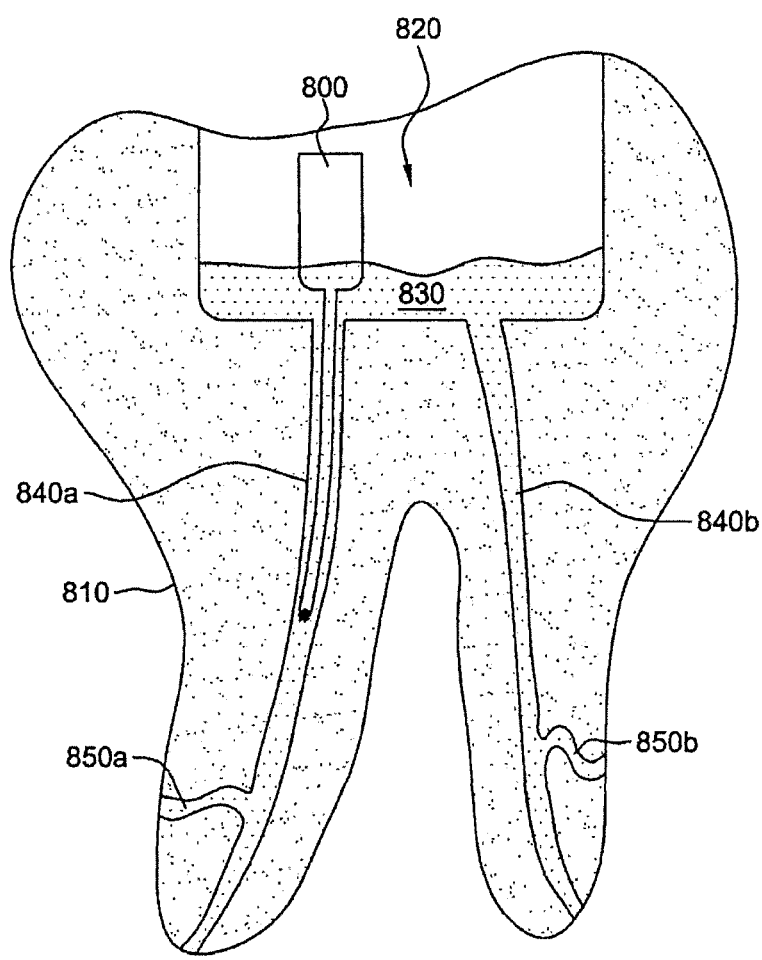
FIG. 8 depicts an aspect of an embodiment of the present invention.
Figure 9:
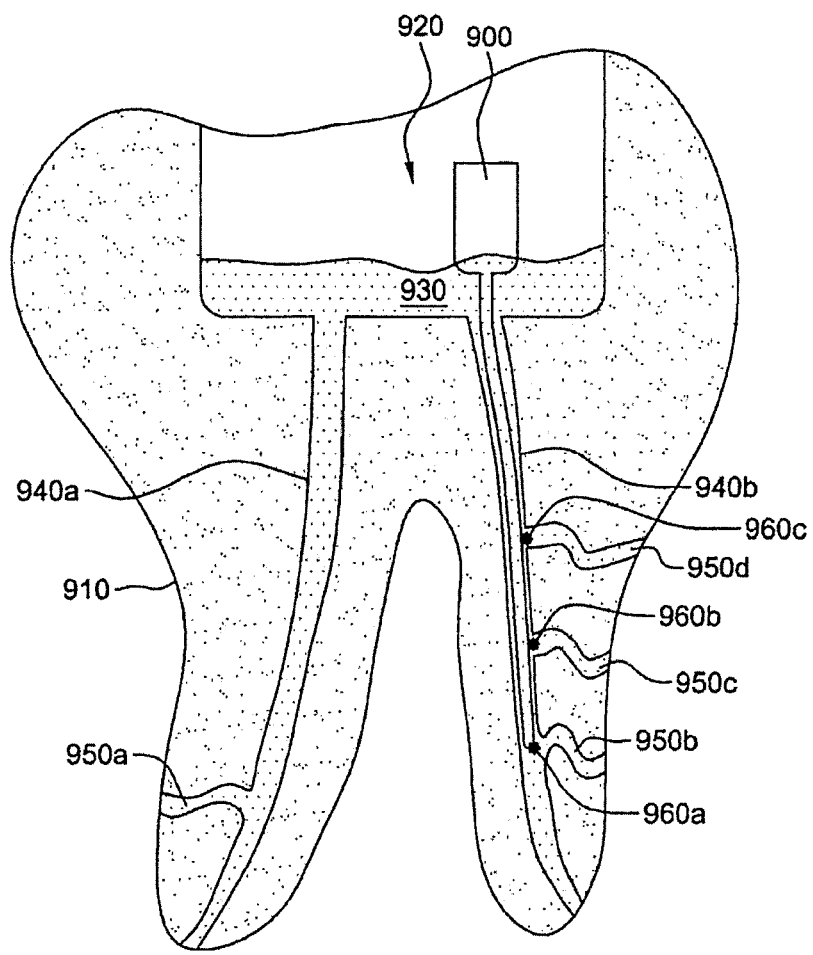
FIG. 9 depicts an aspect of an embodiment of the present invention.

FIGS. 7-9 illustrate the use of an embodiment of the present invention in irrigating canals and dental structures. These figures are merely meant to illustrate some possible positioning of one or more embodiments of the present apparatus during irrigation and are not meant to be exhaustive. One of skill in the art will recognize that the flexibility of the tip presents many possibilities for positioning which would be beneficial for the oral health of a patient.

Referring to FIG. 7, the tip 700 in an embodiment of the apparatus is positioned to fire a discharge at the surface, above the surface, or below the surface of the irrigant's fluid level 730. As discussed earlier, the spark discharge from the tip 700 has an anti-microbial effect even when discharges above the fluid level 730. To position the tip 700, the main coronal chamber 720 of the tooth 710 has been opened surgically. In this figure, both the main canals 740a-740b and lateral canals 750a-750b are visible.

Referring to FIG. 8, the firing tip 800 of an embodiment of the apparatus in placed below the fluid line 830, in fact, the tip 800 is submerged. The tip 800 is being fired in a main canal 840a, but given its flexibility, the tip 800 can also be fired in the vicinity of and/or in the lateral canal 850a.

Referring to FIG. 9, the progression of a tip 900 of an embodiment of the present invention through a main canal 940b wherein it discharges at three different discharge sites 930a-930c, which are adjacent to three lateral canals 950b-950d is shown. The firing tip 900 and probe (not pictured) are moved down the main canal 940b to three lateral canals 950b-950d. As the tip 900 moves up and down the main canal 940b, firing discharges 960a-960c along the laterals 950b-950d, the UV, ozone, shock wave, radicals, and ions pulse directly into the lateral openings for full force and effect. A saline solution is useful in this embodiment because it conducts these particles to their destinations. However, as aforementioned, irrigants that can be used include, but are not limited to, saline solution, glutaraldehyde, and/or any antibiotic and/or anti-microbial solution.

For certain applications of the present invention, pre-treating the water and/or liquid by collecting it in an internal or external reservoir is advantageous. Such applications include, but are not limited to, ultrasonic scalars such as Piezoelectric and/or Magnetostrictive scalars, sonic scalers, and water piks. Meanwhile, for some applications, locating electrodes in the tip is sufficient to treat the water and/or liquid. In embodiments of the present invention utilized as Water Piks, Piezo/Magneto ultrasonic devices, and/or irrigation, including irrigation of periodontic wound sites, the locations of the electrodes utilized to pulse the water and/or liquid include, but are not limited to a reservoir internal or external to the handle of the embodiment of the device, and/or in the tip of the embodiment of the device.

Such applications include, but are not limited to, ultrasonic scalars such as Piezoelectric and/or Magnetostrictive scalars, sonic scalers, and water piks. FIGS. 10-16 are embodiments of the present invention that utilize electrodes in an external reservoir, in an internal reservoir, and/or in the tip of an embodiment of the device to treat the water and/or liquid to be utilized in the intended procedure.

Figure 10:
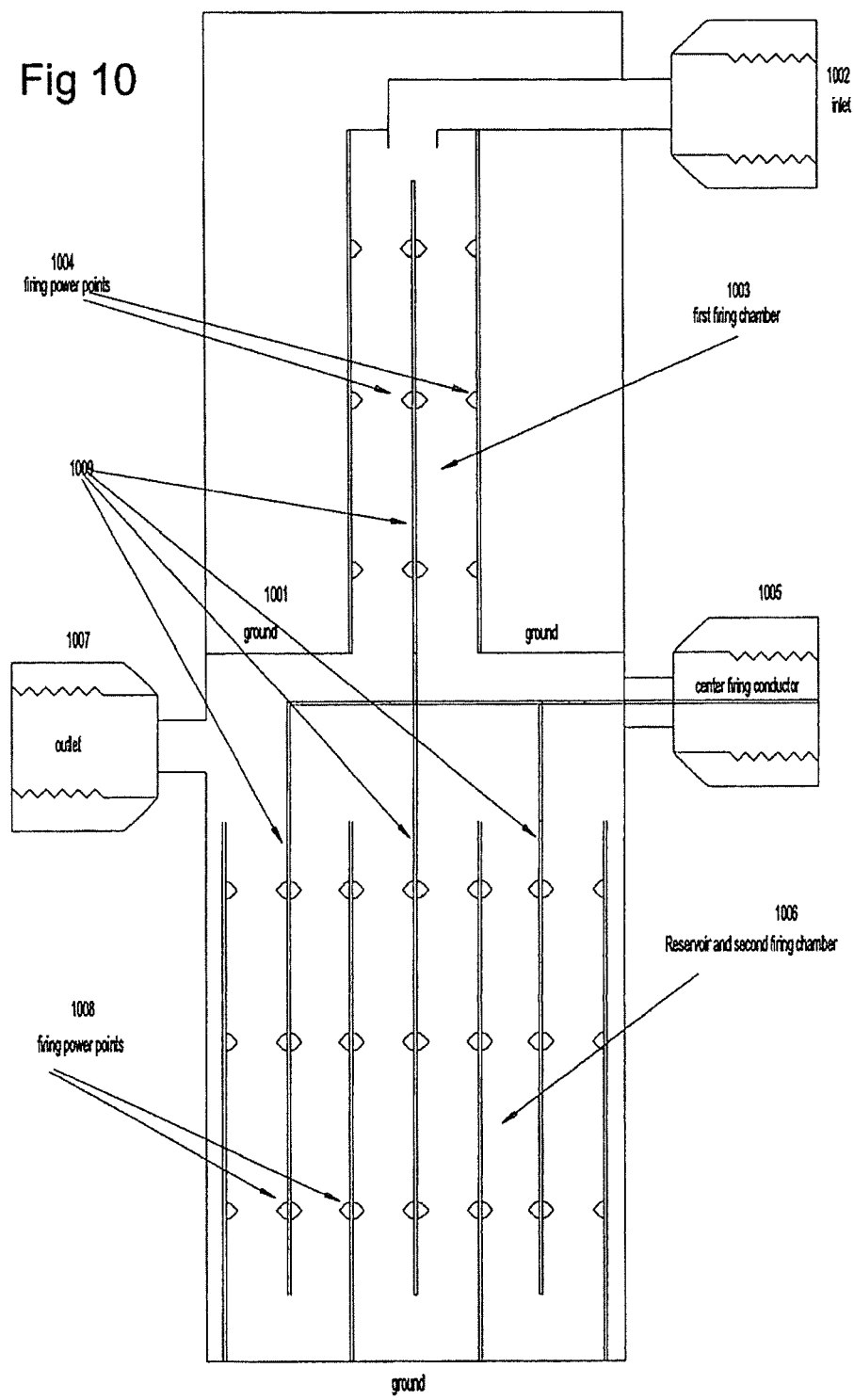
FIG. 10 depicts an aspect of an embodiment of the present invention.

FIG. 10 is an example of a standalone unit embodiment of the present invention that can be utilized as a Piezoelectric and/or Magnetostrictive scalars. Water is moved through the device and while inside, the water is treated through the dispersion of firing discharges, including but not limited to, UV, ozone, shock wave, radicals, and ions pulse. Thus, the water that exits the device carries with it bactericidal benefits. In the embodiment of FIG. 10, water and/or another liquid to be treated with spark discharges is moved through the device from the inlet 1002, and out through the outlet 1007, after being treated with electrical pulses.

In the embodiment of FIG. 10, water is channeled through the inlet 1002, where it progresses into a first firing chamber 1003, which is not storing liquid at this time. Firing points 1004 are positioned throughout this first firing chamber 1003 as well as the second firing chamber 1006. The multiple firing points 1004 save energy consumption because the area within the embodiment can be large. Thus, utilizing multiple firing points 1004 can translate to a cost savings because less energy is required to create the pulse.

The water and/or liquid progresses from the first treatment chamber 1003, into a second firing chamber 1006, which contains a reservoir where the water and/or liquid is stored. The second firing chamber 1006 also contains a group of firing points 1008, distributed within the reservoir. The water and/or liquid is treated by pulsed discharges in this second firing chamber 1006 before it moves through the outlet 1007, which can be understood as a "feed tube" to an used in the irrigation. The firing points 1008 provide the water and/or liquid with exposure to the pulse discharges in an attempt to achieve an 100% pathogen kill before the water and/or liquid leaves the second firing chamber 1006 and into the outlet 1007 to the end of the irrigation device.

In an embodiment of the present invention, the reservoir in the second firing chamber 1006 can be removed from the device and sterilized separately for further bactericidal benefit.

Given that this tip and/or electrode is utilized to treat a reservoir of water and/or liquid, it is also useful for water purification for non-dental health purposes. For example, it can be used to inject bactericidal properties into drinking water as a type of high efficiency filter.

In embodiments of the present invention utilized as Water Piks, Piezo/Magneto ultrasonic devices, and/or irrigation, including irrigation of periodontic wound sites, the locations of the electrodes utilized to pulse the water and/or liquid include, but are not limited to, the first firing chamber 1003, the second firing chamber 1006, and/or a reservoir in the handle of the embodiment of the device. When utilized for ultrasonic uses, an embodiment of the present invention utilizes a reservoir in the handle, rather than in the tip. The description of FIG. 10 can be applied to understand the functionality of the aspects of the embodiments described in FIGS. 11-16.

Figure 11:
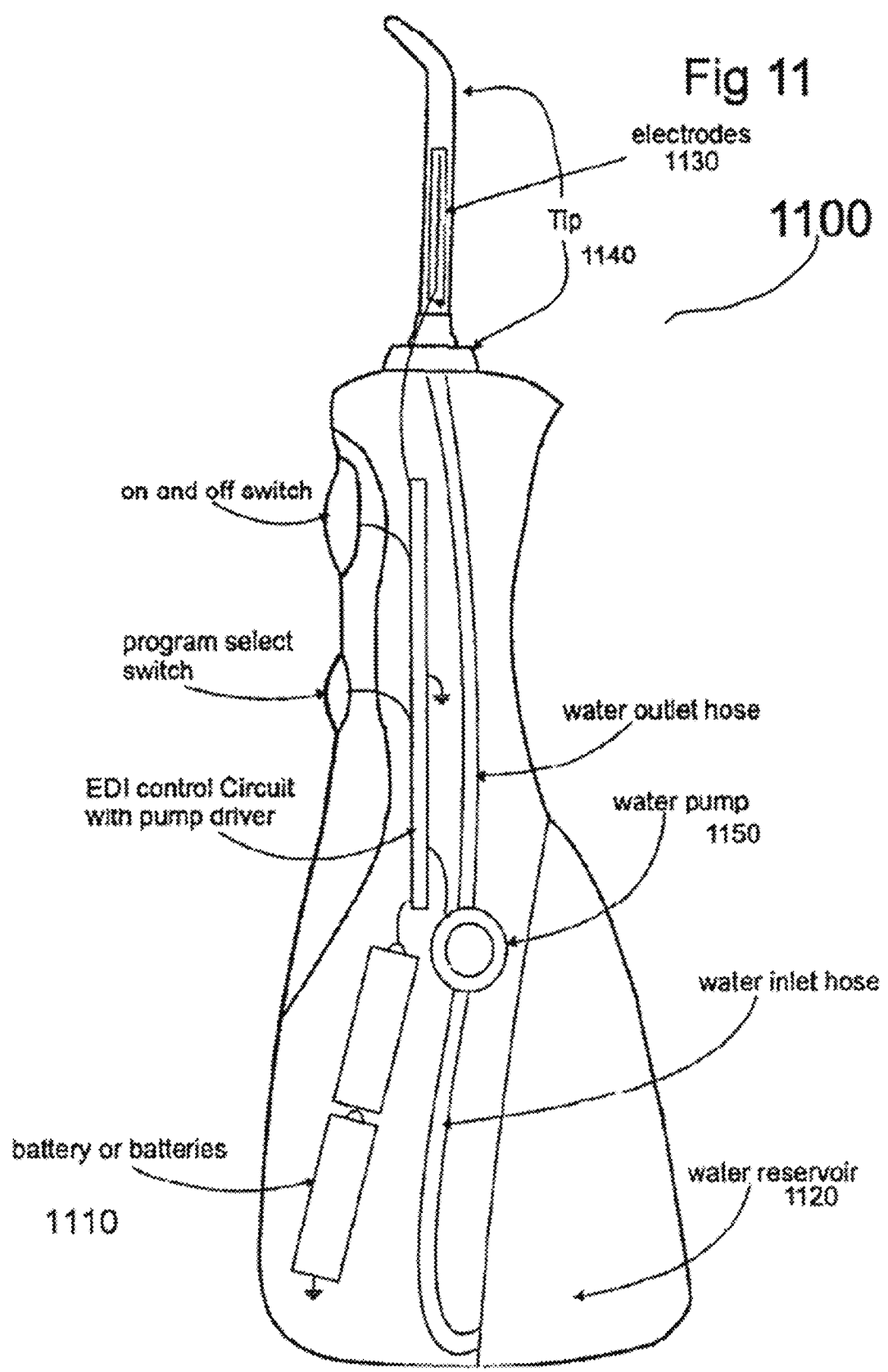
FIG. 11 depicts an aspect of an embodiment of the present invention.

FIG. 11 is an embodiment of the present device 1100 that can be utilized as a water pik, and/or a Piezo/Magneto ultrasonic device. Batteries 1110 serve as the power source in this device 1100. This embodiment of the device 1100 utilizes a single reservoir 1120 for holding and liquid and/or water that will be treated before moves from the tip to the patient's mouth. One set of electrodes 1130 in the tip 1140 of the device 1100 provide the electrical discharge to treat the water and/or liquid before it leaves the tip. The device 1100 is additionally powered by one or more PC boards (not pictured). The water pump 1150 is driven by one or more microcontrollers (not pictured).

In a subset of embodiments of the present invention, such as device 1100, a ceramic conductive substrate can be utilized for the electrodes. This type of electrodes is particularly effective when the water and/or liquid cannot be treated over a period of time in the apparatus, for example, within a reservoir before being released into an area that is being treated. The ceramic conductive electrodes can create a pulse that creates the desired anti-pathogenic effects over a short period of time and when a large volume of water is flowing through an area where the spark discharge is created in a short period of time. In the device 1100, the water and/or liquid is pumped through the tip 1140 and only treated by electrodes in that tip 1140. Thus, there is a short window for the spark discharge.

In another example, in a scalar application, water and/or liquid is pumped through the tip rapidly and under pressure. In an embodiment of the scalar application, a reservoir of water and/or liquid is pumped to different rooms in a dental office. The high volume and pressure flow does not allow for much time to release the spark discharge into the liquid and/or water before it is directed into a treatment area. By using one or more ceramic conductive substrates, the desire pathogen kill rate is achieved within the shortened period of time for a large volume of water and/or liquid with a high pressure.

Figure 12:
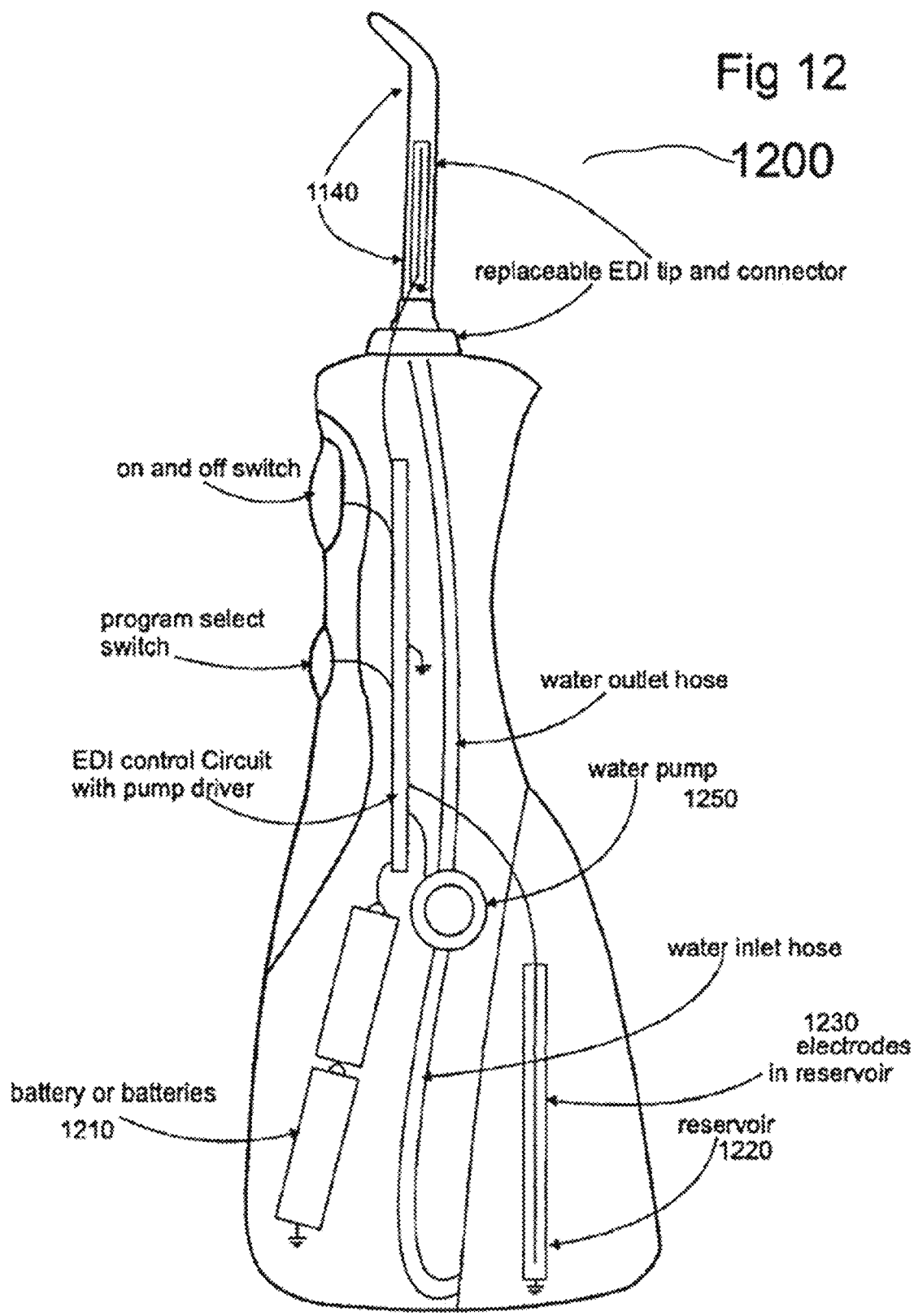
FIG. 12 depicts an aspect of an embodiment of the present invention.

Unlike in the device 1100 of FIG. 11, in FIG. 12, the water and/or liquid to be applied is treated in a reservoir, which allows for a longer treatment time. Similar to FIG. 11, FIG. 12 is an embodiment of the present device 1200 that can be utilized as a water pik, and/or a Piezo/Magneto ultrasonic device, operates on batteries 1210, has a single water reservoir 1220, PC boards (not pictured), a water pump 1250, and is driven by at least one microcontroller (not pictured). However, in this device 1200, the electrodes that provide the spark discharge to treat the water and/or liquid, actually reside in the reservoir 1220. Thus, the amount of time that the electrodes can treat the water and/or liquid is increased.

Figure 13:
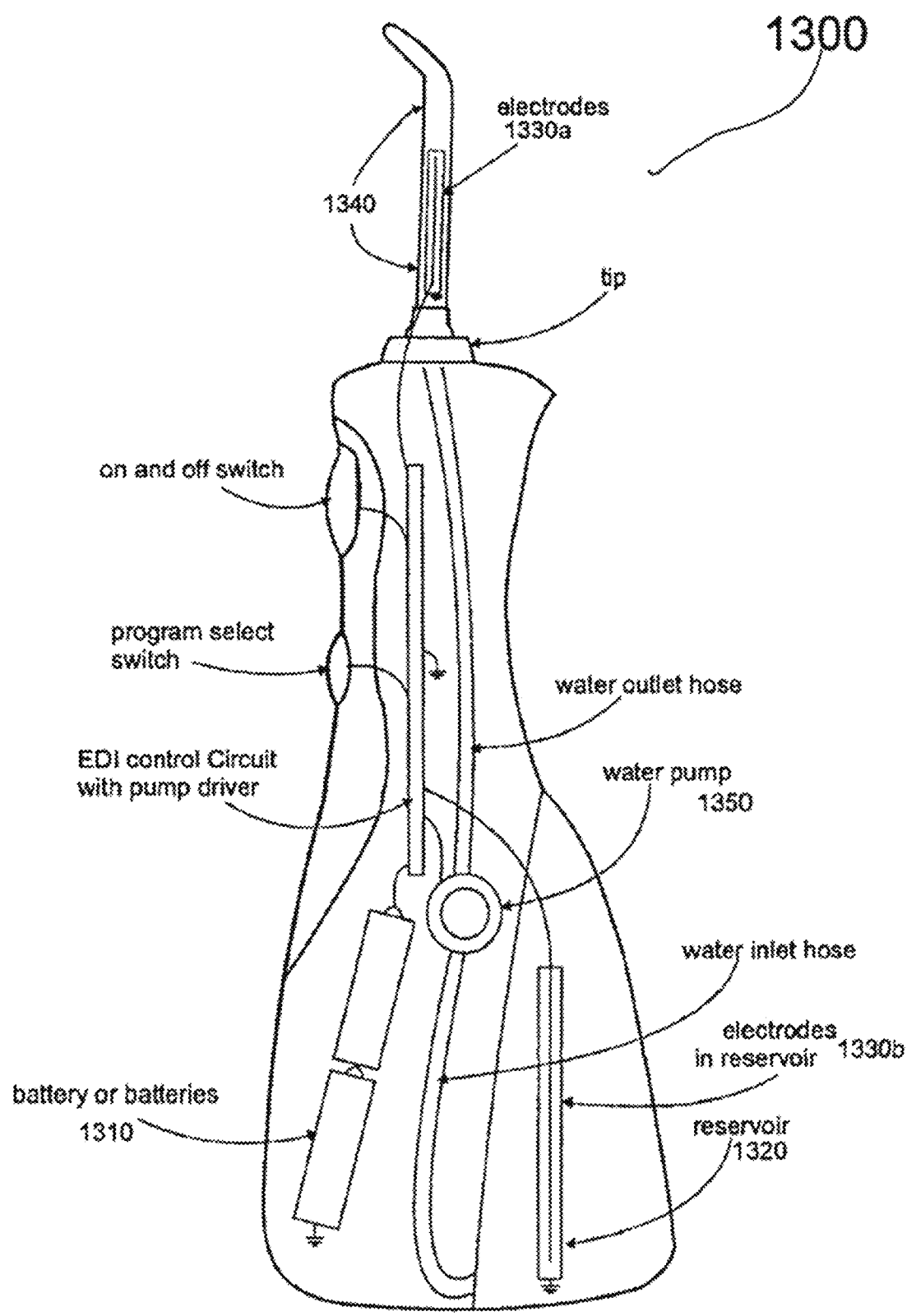
FIG. 13 depicts an aspect of an embodiment of the present invention.

FIG. 13 is another embodiment of a device 1300 that can be utilized as a water pik, and/or a Piezo/Magneto ultrasonic device in accordance with at least one aspect of the present invention. In this embodiment, electrodes discharging the spark pulse to treat water and/or liquid are placed in both the tip 1340 and the reservoir 1320. A first set of electrodes 1330b treats the water and/or liquid while it is in the reservoir 1320, which a second set of electrodes 1330a treats the water and/or liquid as it exists the device 1300.

Figure 14:
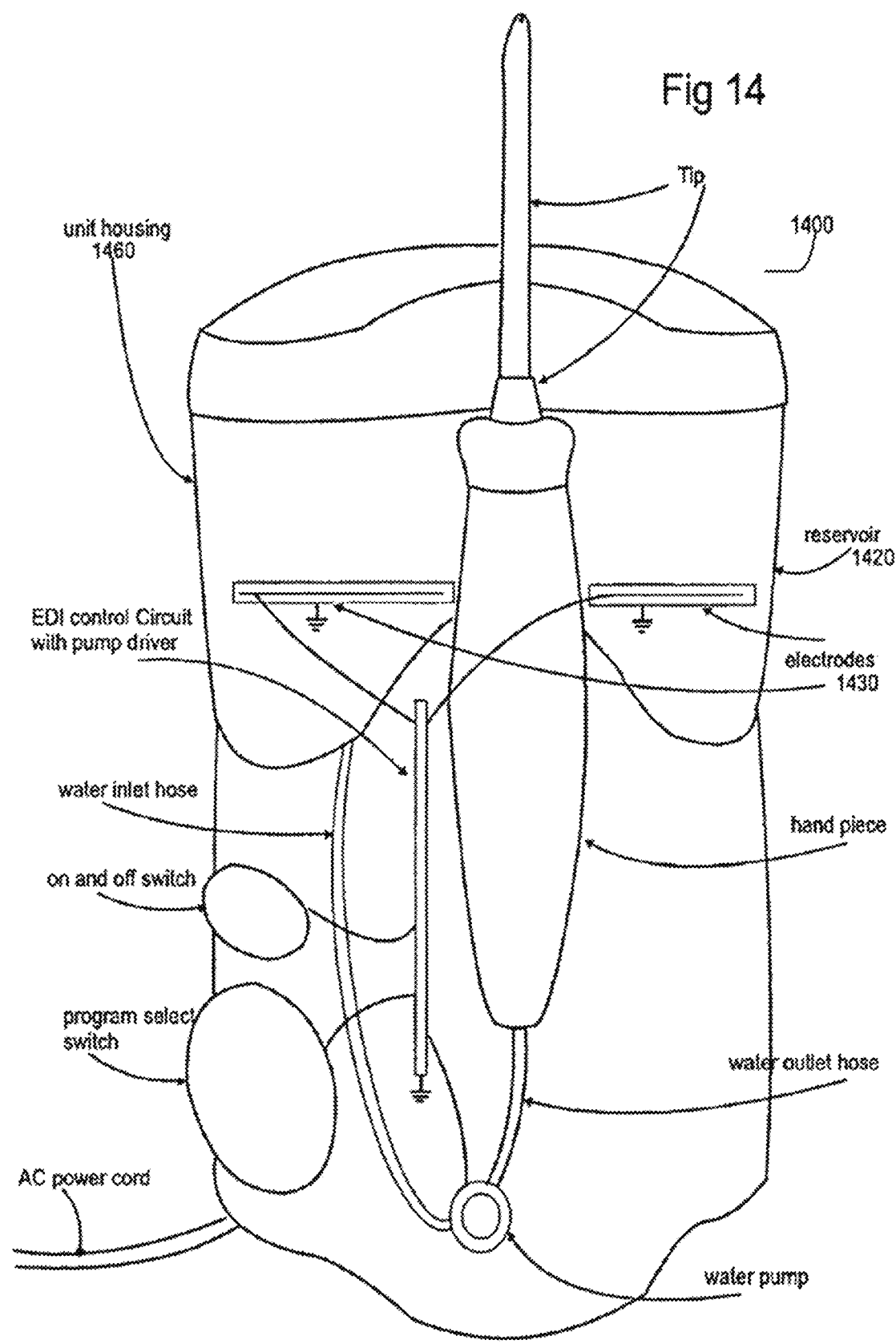
FIG. 14 depicts an aspect of an embodiment of the present invention.
Figure 15:
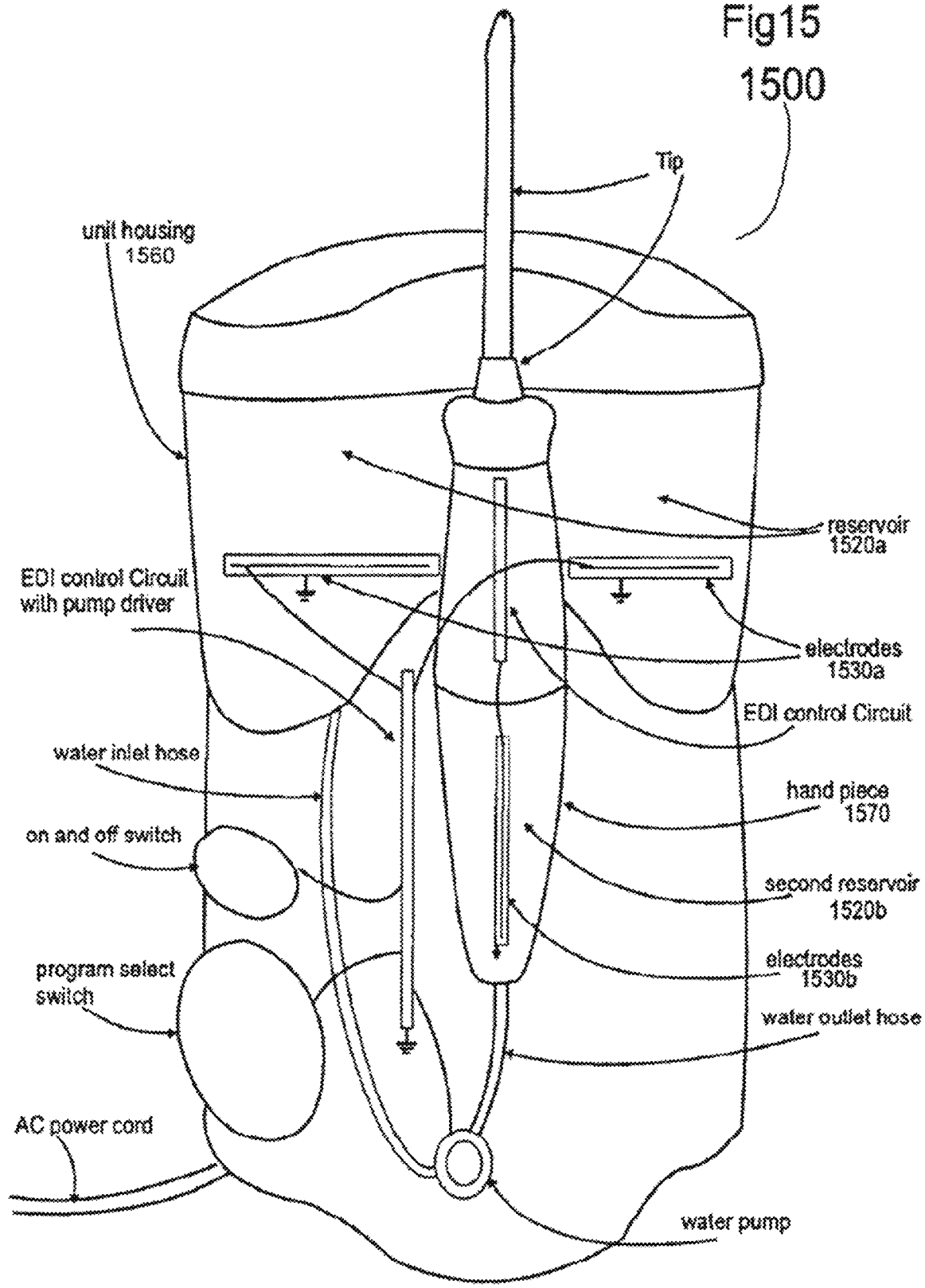
FIG. 15 depicts an aspect of an embodiment of the present invention.
Figure 16:
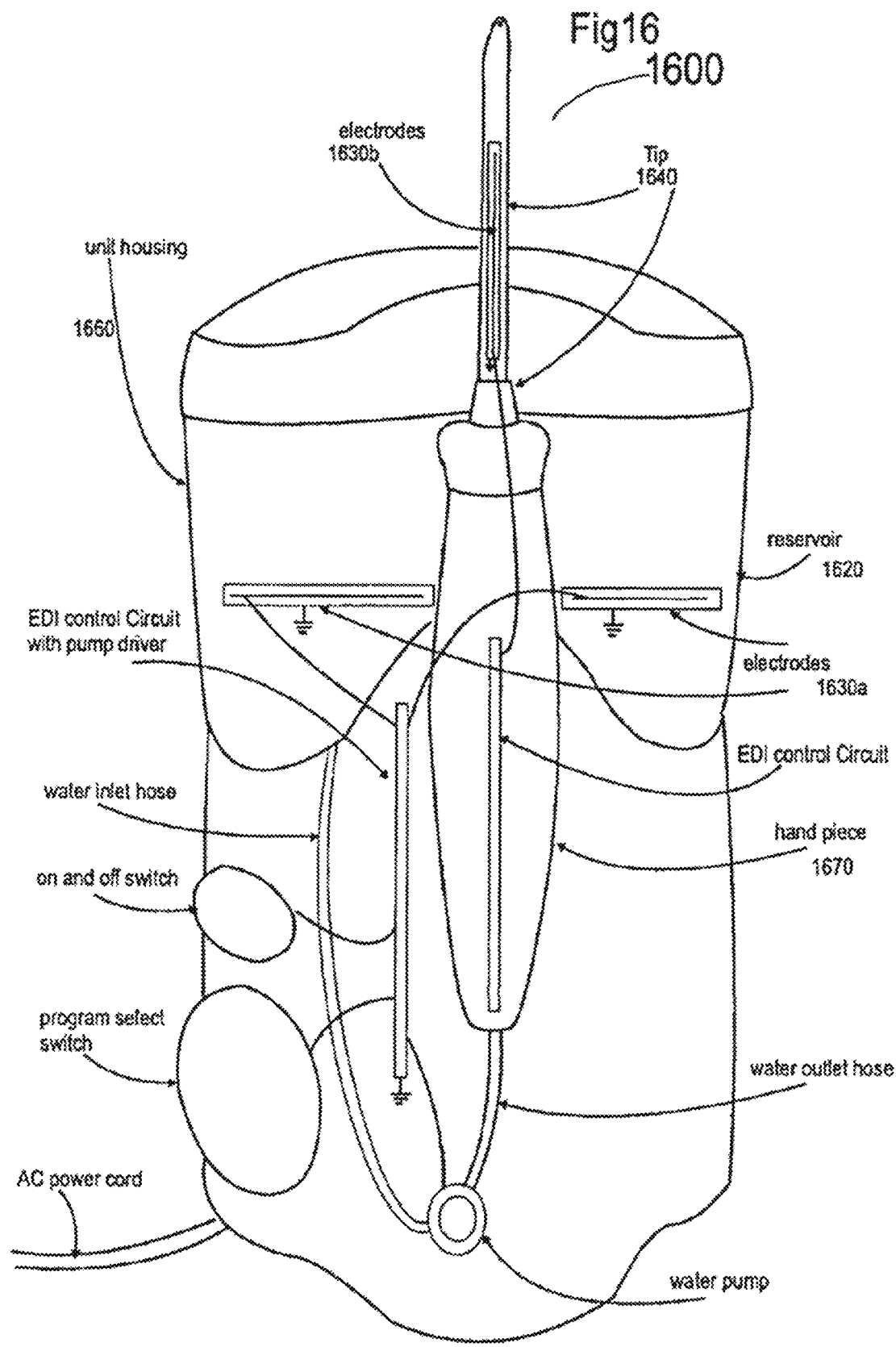
FIG. 16 depicts an aspect of an embodiment of the present invention.

FIGS. 14-16 are embodiments of the present invention that can be utilized as water piks, and/or a Piezo/Magneto ultrasonic devices. However, the devices in FIGS. 14-16 utilize an AC line as a power source and have no batteries. The functionality of these embodiments is discussed in reference to FIGS. 4-5 and FIG. 10. FIG. 14 is an embodiment of the present invention 1400 with one reservoir 1420 in the unit housing 1460 and a set of electrodes in that reservoir 1430. The embodiment 1500 in FIG. 15 has two reservoirs, a first reservoir 1530a in the housing 1560, and a second reservoir 1530b in the hand piece 1570. Thus, the water and/or liquid is treated in the unit housing 1560 and again in the hand piece 1570. The embodiment 1600 in FIG. 16 treats the water and/or liquid twice as well, but rather than utilize a second reservoir in the hand piece 1670, in this embodiment, there is a second set of electrodes 1630b in the tip 1640. This embodiment of the device 1600 also utilizes a first reservoir 1620 with a first set of electrodes 1630a in the unit housing 1660.

FIGS. 11-16 are offered as examples of placements of electrodes with and without reservoirs in embodiments of the present invention and are not meant to be exhaustive. One of skill in the art will recognize that the placement of electrodes and/or reservoirs can vary in accordance with the principles of the present invention.

Figure 17:
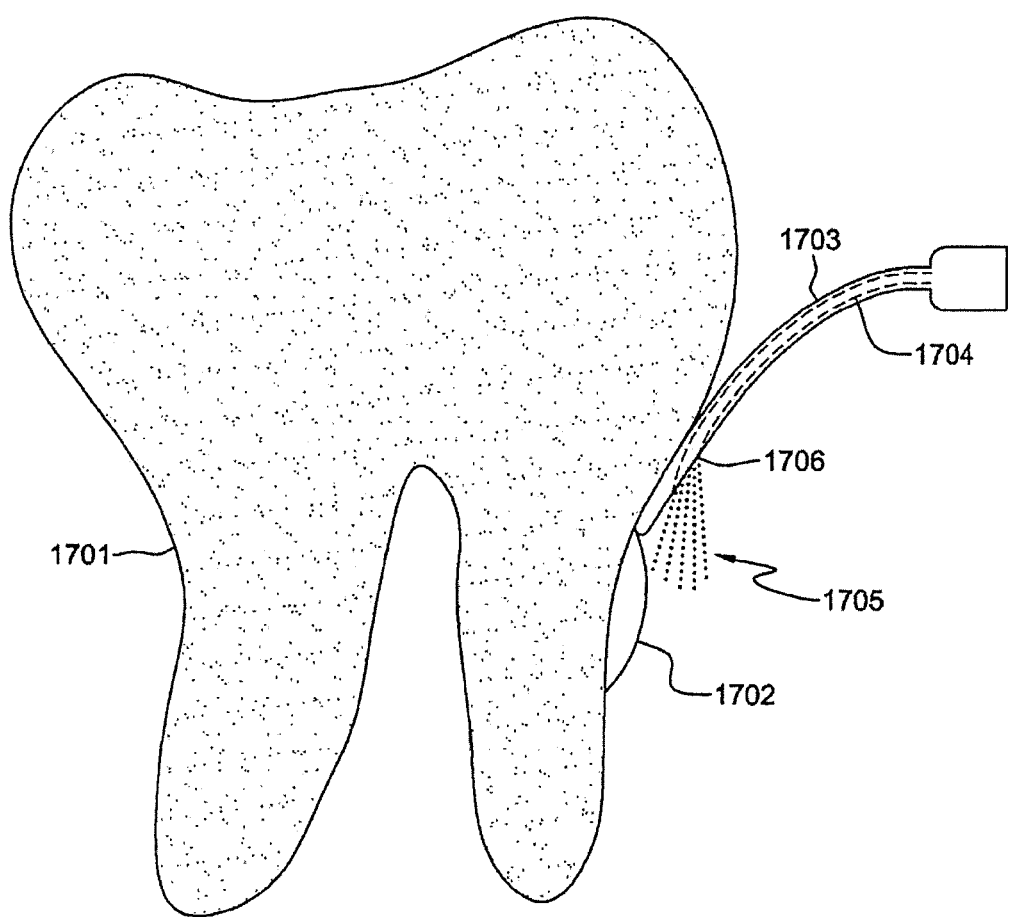
FIG. 17 depicts an aspect of an embodiment of the present invention.

FIG. 17 demonstrates the use of an embodiment of the present application in an ultrasonic procedure. Referring to FIG. 17, a piezo/magneto tip 1703 is being utilized in accordance with the present method to treat the biofilm 1702 on a tooth 1701. Water progresses through the tip 1703 in the internal water line 1704 (which can be seen in FIGS. 11-16). Through the tip 1703, the treated water sprays 1705 from out of the device 1706 (partially pictured). In this embodiment, the water is not treated in the tip 1703, but rather in the hand piece and/or in a reservoir elsewhere in or connected to the device 1706 before it enters the tip 1703 and is utilized on the tooth 1701 and biofilm 1702.

An embodiment of the present invention is utilized in treating all water used in a dental office during various dental procedures. During dental procedures, water is often sprayed into the mouth while simultaneously being suctioned out. It is not desirable to allow a patient to swallow this water because the procedures expose pollutants in the mouth, which can be harmful to the health of the patient, if ingested. However, it is impossible to prevent all the water from being ingested and there may be pathogens in the water because the water system in the area where the dental office is located is not of a high quality. When an individual is being treated whose health is compromised, for example, an elderly patient, the pathogens from the water entering the now-exposed dental structures and/or being ingested by the patient, can harm the general health of this patient. Thus, an embodiment of the present invention can be utilized as part of the delivery system for any water dispensed into the mouth of a patient by a health professional. Embodiments used for this purpose utilize one to many reservoirs so that any dispensed water is treated with a spark discharge before dispensed, even when it is immediately and almost simultaneously suctioned.

An embodiment of the present invention can be used to create a treated water vapor that can be used to mist surfaces in a sanitary environment, such as an operating room. Rather than dispense the treated water/liquid, as fluid, an embodiment of the present invention dispenses the water as a mist, which is applied to surfaces. Because the bactericidal properties of the water and/or liquid that is pulsed with the electric discharge extends beyond the time that it is pulsed, the water/liquid can be used as a cleaning agent in a medical or other setting.

Depending upon the use of the apparatus and the type of pollutant that a user desires to eradicate from a given environment, from a dental canal to a reservoir, the pulse energy and frequency applied will play a role in the kill rate of the embodiment of the apparatus. For example, a pulse rate of up to 1 kJ/pulse with a pulse frequency of 0.01 Hz achieved a total destruction of an *E. coli* colony in water. However, reducing the pulse rate to 0.03 J/pulse had no effect on these microbes. When working to eradicate a population of *Staphylococci*, frequencies of 30 Hz and energy inputs between 12.6 and 25 J/cm$^3$ have been found effective to eradicate an entire colony in water.

Although the present invention has been described in relation to particular embodiments thereof, specifically embodiments that relate to dentistry, many other variations and modifications will become apparent to those skilled in the art. As such, it will be readily evident to one of skill in the art based on the detailed description of the presently preferred embodiment of the apparatus, system and method explained herein, that different embodiments can be realized. For example, an embodiment of the present invention is utilized to purify water, such as water located in the wilderness. This embodiment utilizes a battery or batteries and/or one or more solar cells as a power source. A further embodiment of the present invention is used in place of chlorine to eradicate microbes from a swimming pool. This embodiment is integrated into the swimming pool's existing cleaning system. Because there is no voltage leakage, the water can be enjoyed without fear of electrolysis. This embodiment can also utilize a battery or batteries and/or one or more solar cells as a power source.

Further contemplated integrations for embodiments of the present invention include, but are not limited to, cleaning and sterilizing other dental equipment, integrating an embodiment into a dishwasher for cleaning and disinfecting dishes, integrating an embodiment of the present invention into a home system for safe drinking water, integrating an embodiment into a tool to treat athlete's foot, integrating an embodiment into a disinfecting mop, and/or integrating an embodiment into a shower system that kills staff infections, funguses and other unwanted organic matter.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), and "contain" (and any form contain, such as "contains" and "containing") are open-ended linking verbs. As a result, a method or device that "comprises", "has", "includes" or "contains" one or more steps or elements possesses those one or more steps or elements, but is not limited to possessing only those one or more steps or elements. Likewise, a step of a method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The invention claimed is:

1. An electrical discharge irrigation device, comprising:
   a power source to produce power of a first voltage;
   a circuit coupled to the power source to convert the power of the first voltage to power of a second voltage, wherein the second voltage is higher than the first voltage;
   a trigger to activate the circuit, wherein engaging the trigger discharges a spark into conductive solution such that an acoustical shock wave exits the device through perforated insulating material of an output tip;
   an igniter coupled to the circuit to produce a spike;
   an electrical charge storage component coupled to the igniter, the electrical charge storage component becomes conductive and stores an electrical charge after receiving the spike; and
   the output tip comprising a first electrode with a first charge and an outer layer comprised of the perforated insulating material.

2. The device of claim 1, further comprising a reservoir, wherein the conductive solution is stored in the reservoir.

3. The device of claim 2, the reservoir comprising:
   an inlet and an outlet wherein the conductive solution enters the device through the inlet and exits the device through the outlet, wherein the reservoir further comprises the first electrode, the first electrode receives the electrical charge from the electrical charge storage component.

4. The device of claim 1, wherein the conductive solution enters the output tip through perforations in the insulating material.

5. The device of claim 1, wherein the first electrode and the second electrode are comprised of a biologically inert material.

6. The device of claim 1, wherein the second electrode is a ground electrode.

7. The device of claim 1, wherein the low voltage power source comprises a battery.

8. The device of claim 1, wherein the device is handheld.

9. An electrical discharge irrigation device, comprising:
   a power source to produce power of a first voltage;
   a circuit coupled to the power source to convert the power of the first voltage to power of a second voltage, wherein the second voltage is higher than the first voltage;
   a trigger to activate the circuit;
   an igniter coupled to the circuit to produce a spike;
   an electrical charge storage component coupled to the igniter, where the electrical charge storage component becomes conductive and stores an electrical charge after receiving the spike; and
   a reservoir with an inlet and an outlet wherein a conductive solution enters the device through the inlet and exits the device through the outlet, wherein the reservoir further comprises a first electrode, the first electrode receives the electrical charge from the electrical charge storage component.

10. The device of claim 9, engaging the trigger on the device releases the conductive solution.

11. The device of claim 9, wherein the low voltage power source comprises a battery.

12. The device of claim 9, wherein the first electrode is comprised of a biologically inert material.

13. The device of claim 9, wherein the electrical charge storage component is selected from the group consisting of: an air gap switch and a transformer.

14. The device of claim 9, wherein the power source to produce power of the first voltage comprises a battery.

15. The device of claim 9, further comprising: a handle.

16. The device of claim 15, wherein the reservoir is internal to the handle.

17. The device of claim 15, wherein the reservoir is external to the handle.

* * * * *